(12) United States Patent
Dervisoglu et al.

(10) Patent No.: US 12,109,453 B2
(45) Date of Patent: Oct. 8, 2024

(54) DETECTING OUTDOOR WALKING WORKOUTS ON A WEARABLE DEVICE

(71) Applicant: Apple Inc., Cupertino, CA (US)

(72) Inventors: Gunes Dervisoglu, Santa Clara, CA (US); Hung A. Pham, Oakland, CA (US); Bharath Narasimha Rao, Mountain View, CA (US); Jonathan M. Beard, San Jose, CA (US); Lucie A. Huet, Mountain View, CA (US); Anh N. Phan, Milpitas, CA (US); Vinay R. Majjigi, Mountain View, CA (US); James P. Ochs, San Francisco, CA (US); Karthik Jayaraman Raghuram, Mountain View, CA (US)

(73) Assignee: Apple Inc., Cupertino, CA (US)

( * ) Notice: Subject to any disclaimer, the term of this patent is extended or adjusted under 35 U.S.C. 154(b) by 351 days.

(21) Appl. No.: 17/032,933

(22) Filed: Sep. 25, 2020

(65) Prior Publication Data

US 2021/0093917 A1    Apr. 1, 2021

Related U.S. Application Data

(60) Provisional application No. 62/907,543, filed on Sep. 27, 2019.

(51) Int. Cl.
*A63B 24/00* (2006.01)
*G16H 20/30* (2018.01)
*G16H 40/67* (2018.01)

(52) U.S. Cl.
CPC .......... *A63B 24/0062* (2013.01); *G16H 20/30* (2018.01); *G16H 40/67* (2018.01); *A63B 2220/836* (2013.01); *A63B 2220/89* (2013.01)

(58) Field of Classification Search
CPC . A63B 24/0062; A63B 24/00; A63B 24/0003; A63B 24/0006;
(Continued)

(56) References Cited

U.S. PATENT DOCUMENTS 4,566,461 A   1/1986   Lubell et al.
4,740,009 A   4/1988   Hoelzl
(Continued)

FOREIGN PATENT DOCUMENTS

AU   2008100295 A4   5/2008
CN   102481479 A     5/2012
(Continued)

OTHER PUBLICATIONS

Mattfield, R., Jesch, E., & Hoover, A. (n.d.). A New Dataset for Evaluating Pedometer Performance. IEEE International Conference on Bioinformatics and Biomedicine (BIBM), Clemson, South Carolina, United States of America. https://10.1109/BIBM.2017.8217769 (Year: 2017).*

(Continued)

*Primary Examiner* — Lisa M Caputo
*Assistant Examiner* — Eric Sebastian Von Wald
(74) *Attorney, Agent, or Firm* — Fish & Richardson P.C.

(57) ABSTRACT

Disclosed embodiments include wearable devices and techniques for detecting walking workouts. By accurately and promptly detecting the start of walking workouts activities and automatically distinguishing between walking workout and causal walking activities, the disclosure enables wearable devices to accurately calculate user performance information when users forget to start and/or stop recording walking workouts.

18 Claims, 6 Drawing Sheets

(58) Field of Classification Search
CPC ........ A63B 2024/0009; A63B 24/0021; A63B 2024/0028; A63B 2024/0065; A63B 2024/0071; A63B 2024/0078; A63B 2220/836; A63B 2220/00; A63B 2220/05; A63B 2220/16; A63B 2220/17; A63B 2220/20; A63B 2220/22; A63B 2220/24; A63B 2220/30; A63B 2220/34; A63B 2220/31; A63B 2220/36; A63B 2220/40; A63B 2220/56; A63B 2220/83; A63B 2220/89; G16H 20/30; G16H 40/67; G06K 9/6288; G01C 21/3844; G01C 21/3848; G05B 23/0221; G05B 2219/39155; G05B 2219/40124; G05B 2219/37432; G05B 2219/37134; G08B 21/0446

See application file for complete search history.

(56) References Cited

U.S. PATENT DOCUMENTS

| | | | |
|---|---|---|---|
| 5,158,093 A | 10/1992 | Shvartz et al. |
| 5,663,897 A | 9/1997 | Geiser |
| 5,664,499 A | 9/1997 | Kingsmill |
| 6,013,008 A | 1/2000 | Fukushima |
| 6,059,724 A | 5/2000 | Campbell et al. |
| 6,582,380 B2 | 6/2003 | Kazlausky et al. |
| 6,687,535 B2 | 2/2004 | Hautala et al. |
| 6,837,827 B1 | 1/2005 | Lee et al. |
| 6,862,525 B1 | 3/2005 | Beason et al. |
| 6,868,338 B1 | 3/2005 | Elliott |
| 6,876,947 B1 * | 4/2005 | Darley ............. A61B 5/1118 |
| | | 702/144 |
| 7,254,516 B2 | 8/2007 | Case et al. |
| 7,311,675 B2 | 12/2007 | Peifer et al. |
| 7,377,180 B2 | 5/2008 | Cunningham |
| 7,387,029 B2 | 6/2008 | Cunningham |
| 7,467,060 B2 | 12/2008 | Kulach et al. |
| 7,534,206 B1 | 5/2009 | Lovitt et al. |
| 7,647,196 B2 | 1/2010 | Kahn et al. |
| 7,690,556 B1 | 4/2010 | Kahn et al. |
| 7,771,320 B2 | 8/2010 | Riley et al. |
| 7,805,149 B2 | 9/2010 | Werner et al. |
| 7,841,967 B1 | 11/2010 | Kahn et al. |
| 8,290,480 B2 | 10/2012 | Abramson et al. |
| 8,483,775 B2 | 7/2013 | Buck et al. |
| 8,531,180 B2 | 9/2013 | Piemonte et al. |
| 8,589,174 B2 | 11/2013 | Nelson et al. |
| 8,638,320 B2 | 1/2014 | Harley et al. |
| 8,653,956 B2 | 2/2014 | Berkobin et al. |
| 8,784,271 B2 | 7/2014 | Brumback et al. |
| 8,890,854 B2 | 11/2014 | Tenuta et al. |
| 8,892,391 B2 | 11/2014 | Tu et al. |
| 8,894,576 B2 | 11/2014 | Alwan et al. |
| 8,911,329 B2 | 12/2014 | Lin et al. |
| 8,928,635 B2 | 1/2015 | Harley et al. |
| 9,195,305 B2 | 11/2015 | Markovic et al. |
| 9,264,862 B2 | 2/2016 | Tu et al. |
| 9,413,871 B2 | 8/2016 | Nixon et al. |
| 9,448,250 B2 | 9/2016 | Pham et al. |
| 9,526,430 B2 | 12/2016 | Srinivas et al. |
| 9,704,412 B2 | 7/2017 | Wells et al. |
| 9,737,761 B1 | 8/2017 | Sivaraj |
| 9,788,794 B2 | 10/2017 | Leboeuf et al. |
| 9,817,948 B2 | 11/2017 | Swank et al. |
| 9,918,646 B2 | 3/2018 | Alvarado et al. |
| 9,998,864 B2 | 6/2018 | Kumar et al. |
| 10,098,549 B2 | 10/2018 | Tan et al. |
| 10,154,789 B2 | 12/2018 | Raghuram et al. |
| 10,188,347 B2 | 1/2019 | Self et al. |
| 10,206,627 B2 | 2/2019 | Leboeuf et al. |
| 10,219,708 B2 | 3/2019 | Altini |
| 10,244,948 B2 | 4/2019 | Pham et al. |
| 10,290,260 B2 | 5/2019 | Wu et al. |
| 10,292,606 B2 | 5/2019 | Wisbey et al. |
| 10,512,406 B2 | 12/2019 | Martinez et al. |
| 10,524,670 B2 | 1/2020 | Raghuram et al. |
| 10,620,232 B2 | 4/2020 | Tu et al. |
| 10,687,707 B2 | 6/2020 | Tan et al. |
| 10,687,752 B2 | 6/2020 | Pham et al. |
| 10,694,994 B2 | 6/2020 | Alvarado et al. |
| 10,699,594 B2 | 6/2020 | Mermel et al. |
| 10,617,912 B2 | 7/2020 | Narasimha Rao et al. |
| 10,709,933 B2 | 7/2020 | Tan et al. |
| 11,051,720 B2 | 7/2021 | Perry et al. |
| 11,103,749 B2 | 8/2021 | Mermel et al. |
| 11,278,765 B2 * | 3/2022 | Mohrman ............. G01C 21/166 |
| 11,517,789 B2 | 12/2022 | Xie et al. |
| 2001/0022828 A1 | 9/2001 | Pyles |
| 2002/0019585 A1 | 2/2002 | Dickinson |
| 2003/0032460 A1 | 2/2003 | Cannon et al. |
| 2003/0138763 A1 | 7/2003 | Roncalez et al. |
| 2004/0064061 A1 | 4/2004 | Nissila |
| 2005/0065443 A1 | 3/2005 | Ternes |
| 2005/0107723 A1 | 5/2005 | Wehman et al. |
| 2005/0124906 A1 | 6/2005 | Childre et al. |
| 2005/0212701 A1 | 9/2005 | Nimmo |
| 2006/0046898 A1 | 3/2006 | Harvey |
| 2006/0064277 A1 | 3/2006 | Jung et al. |
| 2006/0136173 A1 | 6/2006 | Case et al. |
| 2006/0190217 A1 | 8/2006 | Lee et al. |
| 2006/0217231 A1 | 9/2006 | Parks et al. |
| 2007/0100666 A1 | 5/2007 | Stivoric et al. |
| 2007/0150229 A1 | 6/2007 | Fujiwara |
| 2007/0219059 A1 | 9/2007 | Schwartz et al. |
| 2007/0275825 A1 | 11/2007 | O'Brien |
| 2007/0276271 A1 | 11/2007 | Chan |
| 2008/0096726 A1 | 4/2008 | Riley et al. |
| 2008/0214360 A1 | 9/2008 | Stirling et al. |
| 2009/0009320 A1 | 1/2009 | O'Connor et al. |
| 2009/0024332 A1 | 1/2009 | Karlov et al. |
| 2009/0043531 A1 | 2/2009 | Kahn et al. |
| 2009/0063099 A1 | 3/2009 | Counts et al. |
| 2009/0143199 A1 * | 6/2009 | Nishibayashi ........ A61B 5/1118 |
| | | 482/8 |
| 2009/0240461 A1 | 9/2009 | Makino et al. |
| 2009/0319221 A1 | 12/2009 | Kahn et al. |
| 2010/0030350 A1 | 2/2010 | House et al. |
| 2010/0030482 A1 | 2/2010 | Li |
| 2010/0130890 A1 | 5/2010 | Matsumura et al. |
| 2010/0184564 A1 | 7/2010 | Molyneux et al. |
| 2010/0204952 A1 | 8/2010 | Irlam et al. |
| 2010/0210953 A1 | 8/2010 | Sholder et al. |
| 2010/0210975 A1 | 8/2010 | Anthony et al. |
| 2010/0217099 A1 | 8/2010 | Leboeuf et al. |
| 2010/0274102 A1 | 10/2010 | Teixeira |
| 2010/0298656 A1 | 11/2010 | McCombie et al. |
| 2011/0040193 A1 | 2/2011 | Seppanen et al. |
| 2011/0054359 A1 | 3/2011 | Sazonov et al. |
| 2011/0082008 A1 | 4/2011 | Cheung et al. |
| 2011/0131012 A1 | 6/2011 | Czaja et al. |
| 2011/0152695 A1 | 6/2011 | Granqvist et al. |
| 2011/0195707 A1 | 8/2011 | Faerber et al. |
| 2011/0238485 A1 | 9/2011 | Haumont et al. |
| 2011/0301436 A1 | 12/2011 | Teixeira |
| 2012/0006112 A1 | 1/2012 | Lee et al. |
| 2012/0083715 A1 | 4/2012 | Yuen et al. |
| 2012/0172677 A1 | 7/2012 | Logan et al. |
| 2012/0238832 A1 | 9/2012 | Jang et al. |
| 2012/0245714 A1 | 9/2012 | Mueller et al. |
| 2012/0296455 A1 | 11/2012 | Ohnemus et al. |
| 2012/0322621 A1 | 12/2012 | Bingham et al. |
| 2013/0006515 A1 | 1/2013 | Vellaikal et al. |
| 2013/0006522 A1 | 1/2013 | Vellaikal et al. |
| 2013/0023739 A1 | 1/2013 | Russell |
| 2013/0041590 A1 | 2/2013 | Burich et al. |
| 2013/0053990 A1 | 2/2013 | Ackland |
| 2013/0073255 A1 | 3/2013 | Yuen et al. |
| 2013/0085861 A1 | 4/2013 | Dunlap |
| 2013/0096943 A1 | 4/2013 | Carey et al. |
| 2013/0135097 A1 | 5/2013 | Doezema |
| 2013/0158686 A1 | 6/2013 | Zhang et al. |
| 2013/0178335 A1 | 7/2013 | Lin et al. |

(56) References Cited

U.S. PATENT DOCUMENTS

| | | |
|---|---|---|
| 2013/0197377 A1 | 8/2013 | Kishi et al. |
| 2013/0218053 A1 | 8/2013 | Kaiser et al. |
| 2013/0267794 A1 | 10/2013 | Fernstrom et al. |
| 2013/0326137 A1 | 12/2013 | Bilange et al. |
| 2013/0340287 A1* | 12/2013 | Stewart ............... A43B 13/184 36/103 |
| 2014/0071082 A1 | 3/2014 | Singh et al. |
| 2014/0073486 A1 | 3/2014 | Ahmed et al. |
| 2014/0087708 A1 | 3/2014 | Kalita et al. |
| 2014/0088444 A1 | 3/2014 | Saalasti et al. |
| 2014/0107932 A1 | 4/2014 | Luna |
| 2014/0109390 A1 | 4/2014 | Manning |
| 2014/0121471 A1 | 5/2014 | Walker |
| 2014/0167973 A1 | 6/2014 | Letchner et al. |
| 2014/0172238 A1 | 6/2014 | Craine |
| 2014/0172361 A1 | 6/2014 | Chiang et al. |
| 2014/0197946 A1 | 7/2014 | Park et al. |
| 2014/0200906 A1 | 7/2014 | Bentley et al. |
| 2014/0207264 A1 | 7/2014 | Quy |
| 2014/0213920 A1 | 7/2014 | Lee et al. |
| 2014/0221854 A1 | 8/2014 | Wai |
| 2014/0228649 A1 | 8/2014 | Rayner et al. |
| 2014/0244071 A1 | 8/2014 | Czaja et al. |
| 2014/0266160 A1 | 9/2014 | Coza |
| 2014/0266789 A1 | 9/2014 | Matus |
| 2014/0276127 A1 | 9/2014 | Ferdosi et al. |
| 2014/0277628 A1 | 9/2014 | Nieminen |
| 2014/0278139 A1 | 9/2014 | Hong et al. |
| 2014/0278229 A1 | 9/2014 | Hong et al. |
| 2014/0279123 A1 | 9/2014 | Harkey et al. |
| 2014/0316305 A1 | 10/2014 | Venkatraman et al. |
| 2014/0348367 A1 | 11/2014 | Vavrus et al. |
| 2015/0066526 A1 | 3/2015 | Cheng et al. |
| 2015/0072712 A1 | 3/2015 | Huang et al. |
| 2015/0087929 A1 | 3/2015 | Rapoport et al. |
| 2015/0088006 A1 | 3/2015 | Rapoport et al. |
| 2015/0100141 A1 | 4/2015 | Hughes |
| 2015/0105096 A1 | 4/2015 | Chowdhury et al. |
| 2015/0119728 A1 | 4/2015 | Blackadar et al. |
| 2015/0147734 A1 | 5/2015 | Flores et al. |
| 2015/0148632 A1 | 5/2015 | Benaron |
| 2015/0173631 A1 | 6/2015 | Richards et al. |
| 2015/0182149 A1 | 7/2015 | Rapoport et al. |
| 2015/0250417 A1 | 9/2015 | Cheng et al. |
| 2015/0256689 A1 | 9/2015 | Erkkila et al. |
| 2015/0260514 A1 | 9/2015 | Menelas et al. |
| 2015/0294440 A1 | 10/2015 | Roberts |
| 2015/0327804 A1 | 11/2015 | Lefever et al. |
| 2015/0328523 A1 | 11/2015 | Heling et al. |
| 2015/0338926 A1 | 11/2015 | Park et al. |
| 2015/0345985 A1 | 12/2015 | Fung et al. |
| 2015/0357948 A1 | 12/2015 | Goldstein |
| 2015/0374240 A1 | 12/2015 | Lee |
| 2016/0021238 A1 | 1/2016 | Abramson et al. |
| 2016/0038083 A1 | 2/2016 | Ding et al. |
| 2016/0054449 A1 | 2/2016 | Pekonen et al. |
| 2016/0057372 A1 | 2/2016 | Iwane et al. |
| 2016/0058302 A1 | 3/2016 | Raghuram et al. |
| 2016/0058329 A1 | 3/2016 | Srinivas et al. |
| 2016/0058332 A1 | 3/2016 | Tan et al. |
| 2016/0058333 A1 | 3/2016 | Arnold et al. |
| 2016/0058356 A1 | 3/2016 | Raghuram et al. |
| 2016/0058370 A1 | 3/2016 | Raghuram et al. |
| 2016/0058371 A1 | 3/2016 | Singh et al. |
| 2016/0058372 A1 | 3/2016 | Raghuram et al. |
| 2016/0059079 A1 | 3/2016 | Watterson |
| 2016/0066859 A1 | 3/2016 | Crawford et al. |
| 2016/0069679 A1 | 3/2016 | Jackson et al. |
| 2016/0084869 A1 | 3/2016 | Yuen et al. |
| 2016/0143579 A1* | 5/2016 | Martikka ............. A61B 5/0205 600/301 |
| 2016/0147319 A1 | 5/2016 | Agarwal et al. |
| 2016/0166178 A1 | 6/2016 | Fuss et al. |
| 2016/0170998 A1 | 6/2016 | Frank et al. |
| 2016/0206248 A1 | 7/2016 | Sartor et al. |
| 2016/0223578 A1 | 8/2016 | Klosinski, Jr. et al. |
| 2016/0242646 A1 | 8/2016 | Obma |
| 2016/0256058 A1 | 9/2016 | Pham et al. |
| 2016/0263435 A1* | 9/2016 | Venkatraman ....... A61B 5/1123 |
| 2016/0269572 A1 | 9/2016 | Erkkila et al. |
| 2016/0287177 A1 | 10/2016 | Huppert et al. |
| 2016/0301581 A1 | 10/2016 | Carter et al. |
| 2016/0314633 A1 | 10/2016 | Bonanni et al. |
| 2016/0361020 A1 | 12/2016 | Leboeuf et al. |
| 2016/0363449 A1 | 12/2016 | Metzler et al. |
| 2016/0374614 A1 | 12/2016 | Cavallaro et al. |
| 2017/0007166 A1 | 1/2017 | Roovers et al. |
| 2017/0061817 A1 | 3/2017 | Mettler May |
| 2017/0074897 A1 | 3/2017 | Mermel et al. |
| 2017/0082649 A1 | 3/2017 | Tu et al. |
| 2017/0094450 A1 | 3/2017 | Tu et al. |
| 2017/0111768 A1 | 4/2017 | Smith et al. |
| 2017/0181644 A1 | 6/2017 | Meer et al. |
| 2017/0182360 A1 | 6/2017 | Chang et al. |
| 2017/0188893 A1 | 7/2017 | Venkatraman et al. |
| 2017/0202486 A1 | 7/2017 | Martikka et al. |
| 2017/0211936 A1 | 7/2017 | Howell et al. |
| 2017/0242499 A1 | 8/2017 | Shah et al. |
| 2017/0242500 A1 | 8/2017 | Shah et al. |
| 2017/0251972 A1 | 9/2017 | Jayaraman et al. |
| 2017/0259116 A1 | 9/2017 | Mestas |
| 2017/0269734 A1 | 9/2017 | Graff |
| 2017/0269785 A1 | 9/2017 | Abdollahian et al. |
| 2017/0273619 A1 | 9/2017 | Alvarado et al. |
| 2017/0347885 A1 | 12/2017 | Tan et al. |
| 2017/0357007 A1 | 12/2017 | Miller et al. |
| 2017/0367658 A1 | 12/2017 | LeBoeuf et al. |
| 2017/0368413 A1 | 12/2017 | Shavit |
| 2018/0028863 A1 | 2/2018 | Matsuda |
| 2018/0043210 A1 | 2/2018 | Niehaus et al. |
| 2018/0049694 A1 | 2/2018 | Singh Alvarado et al. |
| 2018/0050235 A1 | 2/2018 | Tan et al. |
| 2018/0055375 A1 | 3/2018 | Martinez et al. |
| 2018/0055439 A1 | 3/2018 | Pham et al. |
| 2018/0056123 A1 | 3/2018 | Narasimha Rao et al. |
| 2018/0056128 A1 | 3/2018 | Narasimha Rao et al. |
| 2018/0056129 A1 | 3/2018 | Narasimha Rao et al. |
| 2018/0249908 A1 | 9/2018 | Anthony et al. |
| 2018/0279914 A1 | 10/2018 | Patek et al. |
| 2018/0303381 A1 | 10/2018 | Todd et al. |
| 2018/0344217 A1 | 12/2018 | Perry et al. |
| 2019/0038938 A1 | 2/2019 | Nagasaka et al. |
| 2019/0076063 A1 | 3/2019 | Kent et al. |
| 2019/0090087 A1* | 3/2019 | Taylor .................. H04W 4/023 |
| 2019/0184230 A1 | 6/2019 | Lee et al. |
| 2019/0184233 A1 | 6/2019 | Xie et al. |
| 2019/0360813 A1* | 11/2019 | Zhao ..................... G01C 21/188 |
| 2020/0232796 A1* | 7/2020 | Lee ............................ G01P 15/18 |
| 2021/0068689 A1 | 3/2021 | Ochs et al. |
| 2021/0068712 A1 | 3/2021 | Humblet et al. |
| 2021/0068713 A1 | 3/2021 | Dervisoglu et al. |
| 2021/0093918 A1 | 4/2021 | Dervisoglu et al. |
| 2022/0114873 A1 | 4/2022 | Williams |
| 2022/0241641 A1 | 8/2022 | Mermel et al. |

FOREIGN PATENT DOCUMENTS

| | | | |
|---|---|---|---|
| CN | 104218976 A | 12/2014 | |
| CN | 105031905 A | 11/2015 | |
| CN | 105068656 A | 11/2015 | |
| GB | 2465824 A | 6/2010 | |
| IN | 259/KOL/2015 | 12/2015 | |
| JP | 2004089317 A * | 3/2004 | ......... A61B 5/02438 |
| JP | 2010-051333 A | 3/2010 | |
| JP | 2013-039316 A | 2/2013 | |
| JP | 2014-042757 A | 3/2014 | |
| JP | 2016-150018 A | 8/2016 | |
| JP | 2018-000543 A | 1/2018 | |
| JP | 2018-015187 A | 2/2018 | |
| JP | 2019028796 A * | 2/2019 | |
| JP | 2020148558 A * | 9/2020 | |
| RO | 122807 B1 | 2/2010 | |
| WO | 03/61779 A1 | 7/2003 | |
| WO | 2010/090867 A2 | 8/2010 | |

(56) References Cited

FOREIGN PATENT DOCUMENTS

| WO | 2011/105914 A1 | 9/2011 | | |
|---|---|---|---|---|
| WO | 2015/126182 A1 | 8/2015 | | |
| WO | 2015/200900 A1 | 12/2015 | | |
| WO | 2016/044831 A1 | 3/2016 | | |
| WO | 2016/073620 A1 | 5/2016 | | |
| WO | WO-2016142246 A2 | * | 9/2016 | ......... G06F 19/3481 |
| WO | WO-2018117914 A1 | * | 6/2018 | ............... A61B 5/11 |

OTHER PUBLICATIONS

"Your Fitness FAQ, Why is it important to warm up and cool down in a workout?", 2012, Web, Retrieved from: http://www.yourfitnessfaq.com/whyisitimportanttowarmupandcooldowninaworkout.html.

Bo et al, "TEXIVE: Detecting Drivers Using Personal Smart Phones by Leveraging Inertial Sensors," Department of ComputerScience, Illinois Institute of Technology, Chicago IL, Dec. 7, 2014, pp. 1-12.

Brooks, G.A. et al., "Exercise Physiology: Human Bioenergetics and Its Applications," Fourth Edition, McGraw Hill, ISBN 0-07-255642-0, Chapter 2: Bioenergetics, Chapter 10: Metabolic Response to Exercise: Lactate Metabolism During Exercise and Recovery, Excess Postexercise 02 Consumption (EPOC), O2 Deficit, O2 Debt, and the Anaerobic Threshold, Chapter 16: Cardiovascular Dynamics During Exercise, Chapter 21: Principles of Endurance Conditioning, Chapter 27: Exercise Testing and Prescription, 141 pages (2004).

Bruce, RA et al., "Exercising testing in adult normal subjects and cardiac patients," Pediatrics, vol. 32, No. Suppl., pp. 742-756 (Oct. 1963).

Bruce, RA et al., "Maximal oxygen intake and nomographic assessment of functional aerobic impairment in cardiovascular disease," American Heart Journal, vol. 85, Issue 4, pp. 546-562 (Apr. 1973).

Burke, Edmund R., "High-Tech Cycling," Second Edition, Human Kinetics, Chapter 4: Optimizing the Crank Cycle and Pedaling Cadence, Chapter 5: Cycling Biomechanics, Chapter 6: Cycling Power, Chapter 10: Physiology of Professional Road Cycling, Chapter 11: Physiology of Mountain Biking, 131 pages (2003).

Cavanagh, P.R. et al., "The effect of stride length variation on oxygen uptake during distance running," Medicine and Science in Sports and Exercise, vol. 14, No. 1, pp. 30-35 (1982).

Chu, "In-Vehicle Driver Detection Using Mobile Phone Sensors", Submitted for Graduation with departmental Distinction in Electrical and Computer Engineering, Apr. 20, 2011, pp. 1-21.

Earnest, C.P. et al., "Cross-sectional association between maximal estimated cardiorespiratory fitness, cardiometabolic risk factors and metabolic syndrome for men and women in the Aerobics Center Longitudinal Study," Mayo Clin Proceedings, vol. 88, No. 3, pp. 259-270, 20 pages (Mar. 2013).

Fox, S.M. et al., "Physical Activity and the Prevention of Coronary Heart Disease," Bull. N.Y. Acad. Med., vol. 44, No. 8, pp. 950-967 (Aug. 1968).

Frankenfield et al., "Comparison of Predictive Equations for Resting Metabolic Rate in Healthy Nonobese and Obese adults: A systematic review. Journal of the American Dietetic Association", May 2005, vol. 105, No. 5, p. 775-789.

Gao et al., "Evaluation of accelerometer based multi-sensor versus single-sensor activity recognition systems", Medical engineering & physics 36.6 (2014): 779-785.

Glass et al., "ACSM's Metabolic Calculations Handbook," Lippincott Williams & Wilkins, 124 pages (2007).

Hasson et al., "Accuracy of four resting metabolic rate production equations: Effects of sex, body mass index, age, and race/ethnicity", Journal of Science and Medicine in Sport, 2011, vol. 14, p. 344-351.

Human Kinetics, Aerobic Workout Components, 2011, Web, Retrieved from: http://www.humankinetics.com/excerpts/excerpts/aerobicworkoutcomponentsexcerpt.

International Search Report and Written Opinion received for POT Patent Application No. PCT/US2018/047290, mailed on Nov. 8, 2018, 14 pages.

Isaacs et al, "Modeling energy expenditure and oxygen consumption in human exposure models: accounting for fatigue and EPOC", 2008, Journal of Exposure Science and Environmental Epidemiology, 18: 289-298.

Jackson et al., "Prediction of functional aerobic capacity without exercise testing, Medicine and Science in Sports and Exercise", 22(6), 863-870, 1990.

Keytel et al, "Prediction of energy expenditure from heart rate monitoring during submaximal exercise", Journal of Sports Sciences, 23(3), 2005: 289-297.

KINprof, 2011, Predictive VO2max tests, Web Video, Retrieved from: https://www.youtube.com/walch?v =_9e3HcYIsm8.

Kunze et al. "Where am i: Recognizing on-body positions of wearable sensors." Location-and context-awareness. Springer Berlin Heidelberg, 2005. 264-275.

Kyle, Chester R., "Reduction of Wind Resistance and Power Output of Racing Cyclists and Runners Travelling in Groups", Ergonomics, vol. 22, No. 4, 1979, pp. 387-397.

Lavie et al., "Impact of cardiorespiratory fitness on the obesity paradox in patients with heartfailure," Mayo Clinic Proceedings, vol. 88, No. 3, pp. 251-258 (Mar. 2013).

Le, et al., "Sensor-based Training Optimization of a Cyclist Group", Seventh International Conference on Hybrid Intelligent Systems, IEEE 2007, pp. 265-270.

Lucas et al, "Mechanisms of orthostatic intolerance following very prolonged exercise", 2008, J. Appl. Physiol., 105: pp. 213-225.

Margaria, R. et al., "Energy cost of running," Journal of Applied Physiology, vol. 18, No. 2, pp. 367-370 (Mar. 1, 1963).

McArdle, W.D. et al., "Exercise Physiology: Nutrition, Energy and Human Performance," Seventh t:amon, Lippincott Williams & Wilkins, Chapter 5: Introduction to Energy Transfer, Chapter 6: Energy Transfer in the Body, Chapter 7: Energy Transfer During Exercise, Chapter 8: Measurement of Human Energy Expenditure, Chapter 9: Human Energy Expenditure During Rest and Physical Activity, Chapter 10: Energy Expenditure During Walking, Jogging, Running and Swimming, Chapter 11: Individual Differences and Measurement of Energy Capacities, Chapter 21: Training for Anaerobic and Aerobic Power.

Myers et al., "Exercise Capacity and Mortality Among Men Referred for Exercise Testing," The New England Journa of Medicine, vol. 346, No. 11, pp. 793-801 {Mar. 14, 2002).

Noakes, Timothy D., "Lore of Running," Fourth Edition, Human Kinetics, Chapter 2: Oxygen Transport and Running Economy, Chapter 3: Energy Systems and Running Performance, 157 pages (2002).

Novatel, "IMU Error and Their Effects", Novatel Application Notes APN-064 Rev A p. 1-6, Feb. 21, 2014.

PCT International Application No. PCT/US2017/049693, International Search Report and Written Opinion dated Aug. 12, 2017.

Rapoport, Benjamin I., "Metabolic Factors Limiting Performance in Marathon Runners," PloS Computational Biology, vol. 6, Issue 10, 13 pages (Oct. 2010).

Rowlands et al. "Assessing Sedentary Behavior with the GENEActiv: Introducing the Sedentary Sphere", Medicine and science in sports and exercise, 46.6 (2014), pp. 1235-1247.

Sabatini, "Kalman-filter-based orientation determination using inertial/magnetic sensors: observability analysis and performance evaluation", Sep. 27, 2011, Sensors 2011, 11, 9182-9206.

Song et al., "Training Activity Recognition Systems Online Using Real-Time Crowdsourcing", University of Rochester Computer Science, UbiCom' 12, Sep. 5-8, 2012 (2 pages).

Tanaka, H. et al., "Age-predicted maximal heart rate revisited," Journal of the American College of Cardiology, vol. 37, Issue 1, pp. 153-156 (Jan. 2001).

Vella et al, Exercise After-Burn: Research Update, 2005, Web, Retrieved from: http://www.unm.edu/~lkravilz/Article%20folder/epocarticle.html.

Wang et al., "Time constant of heart rate recovery after low level exercise as a useful measure of cardiovascular fitness," Cont. Proc. IEEE Eng. Meda Biol. Soc., vol. 1, pp. 1799-1802: (2006).

Yamaji, et al (Relationship Between Heart Rate and Relative Oxygen Intake in Male Subjects Aged 10 to 27 Years, 1978, J. Human Ergol., 7:29-39) (Year: 1978).

(56) References Cited

OTHER PUBLICATIONS

U.S. Appl. No. 17/015,912, filed Sep. 9, 2020, Humblet et al.
U.S. Appl. No. 17/015,965, filed Sep. 9, 2020, Dervisoglu et al.
U.S. Appl. No. 17/016,020, filed Sep. 9, 2020, Ochs et al.
Alexander, "Energetics and Optimization of Human Walking and Running," Am J Human Biology, Mar. 20, 2002, 14:641-648.
Lasecki, "Real-Time Crowd Labeling for Deployable Activity Recognition," University of Rochester Computer Science, Feb. 23, 2013, 10 pages.
Latt et al., "Walking speed, cadence and step length are selected to optimize the stability of head and pelvis accelerations," Experimental Brain Research, Aug. 24, 2007, 184: 201-209.
Morgan et al., "Effect of step length optimization on the aerobic demand of running," Journal of Applied Physiology, 1994, 245-251.
PCT International Preliminary Report on Patentability in International Appln. No. PCT/US2017/049693, dated Mar. 5, 2019, 8 pages.
PCT International Preliminary Report on Patentability in International Appln. No. PCT/US2018/047290, dated Mar. 17, 2020, 9 pages.
Pfitzinger.com "Optimal Marathon Training Sessions, Distance Coach. com, Intelligent Training for Distance Runners," archived May 15, 2012, <https://web.archive.org/web/20120515081237/http://www.pfitzinger.com/marathontraining.shtml>, printed Jan. 20, 2017, 3 pages.
Romijn et al., "Regulation of endogenous fat and carbohydrate metabolism in relation to exercise intensity and duration," Am. J. Physiol., 1993, 6:1-13.
Triendurance.com "Running with a Higher Cadence, Triendurance," Oct. 23, 2021, retrieved from <https://web.archive.org/web/20080228162904/http://www.trienduranee.com/Related.asp?PageID=14&NavID=7>, 2 pages.
Zhao, "New Developments of the Typical MEMS and Wearable Sensor Technologies," Micronanoelectronic Technology, Jan. 2015, 52(1):1-13 (with English abstract).
Zhou et al., "Development of the Technical Monitoring System for Swimming Competition," China Sport Science and Technology, Aug. 2008, 44(4):84-86 (with English abstract).
Shen et al., "MiLift: Efficient Smartwatch-Based Workout Tracking Using Automatic Segmentation," IEEE Transactions on Mobile Computing, Jul. 2018, 17(7):1609-1622.
Unuma et al., JP2007093433, published on Apr. 12, 2007, 27 pages (machine translated English version).
Kodama et al., Examination of Inertial Sensor-Based Estimation Methods of Lower Limb Joint Moments and Ground Reaction Force: Results for Squat and Sit-to-Stand Movements in the Sagittal Plane, Aug. 1, 2016, Sensors 2016, pp. 1-19 (Year: 2016).

\* cited by examiner

DETECTING OUTDOOR WALKING WORKOUTS ON A WEARABLE DEVICE

CROSS REFERENCE TO RELATED APPLICATIONS

This application claims the benefit of U.S. Provisional Application Ser. No. 62/907,543 filed Sep. 27, 2019, the entire contents of which is hereby incorporated by reference.

FIELD

The present disclosure relates generally to detecting outdoor walking workouts using a wearable device.

BACKGROUND

A wearable device may be worn on the hand, wrist, or arm of a person when walking. It may be desirable to track outdoor walking workouts on a wearable device to promote exercise and for other health related reasons. Detecting the start of a walking workout and distinguishing walking workouts from other walking activities are essential components of accurately tracking outdoor walking workouts.

The present disclosure is related to other methods of detecting the activities on a wearable device. Specifically, U.S. patent application Ser. No. 17/015,965, filed on Sep. 9, 2020. and entitled "DETECTING SWIMMING ACTIVITIES ON A WEARABLE DEVICE". which patent application is incorporated herein in its entirety.

SUMMARY

In one aspect, disclosed herein are computer implemented methods for improving performance of a wearable device while recording a walking activity comprising: receiving motion data of a user from a motion sensing module of the wearable device; counting, by one or more processor circuits of the wearable device, user steps based on the motion data; detecting, by the one or more processor circuits, a bout based on the user steps, the bout comprising a collection of continuous steps; estimating, by the one or more processor circuits, user mechanical work performed during the bout; detecting, by the one or more processor circuits, the start of a walking activity, the detecting the start of the walking activity comprising: comparing the user mechanical work to a mechanical work threshold; in response to detecting a value for the user mechanical work below the mechanical work threshold, classifying movement performed by the user based on motion data; and in response to classifying the movement performed by the user as a patterned movement, starting a walking activity; and sending, by the one or more processor circuits, a notification to the user requesting confirmation of the start of the walking activity.

In one aspect, the method comprises: receiving, pressure data, from a pressure sensor of the wearable device; receiving, location data, from a GPS module of the wearable device; calculating, by the one or more processor circuits, a grade for each step included in the user steps based on the pressure data, the grade measuring steepness of terrain stepped on during the bout; calculating, by the one or more processor circuits, a step distance for each step included in the bout based on the motion data and the location data; calculating, by the one or more processor circuits, a bout time describing the bout's duration; and estimating, by the one or more processor circuits, the user mechanical work performed during the bout based on the step distance, the grade, and the bout time.

In one aspect, the method comprises: estimating, by the one or more processor circuits, a device heading at every step included in the bout based on the motion data, the device heading describing the orientation of the wearable device relative to a frame of reference; determining, by the one or more processor circuits, a user direction of travel based on the device heading and the step count; and classifying movement performed during the bout based on the user direction of travel.

In one aspect, motion data comprises acceleration data obtained from an accelerometer and gyroscope data obtained from a gyroscope. In one aspect, the patterned movement is a straight movement pattern or a repetitive movement pattern, wherein the straight movement pattern has few changes in user direction and the repetitive movement pattern has changes in user direction that repeat at regular intervals during the walking activity. In one aspect, the notification is a notification UI displayed on a display screen of the wearable device.

In one aspect, the method comprises: distinguishing between a walking workout and a casual walking activity based on the comparing the user mechanical work to the user mechanical work threshold and the classifying the movement performed by the user. In one aspect, the method comprises: in response to starting the walking activity, calculating user performance information during the walking activity; and detecting the end of the walking workout based the user performance information.

In one aspect, the mechanical work threshold is specific to the user. In one aspect, the method comprises calculating, by the one or more processor circuits, load based on the grade and the user steps, the load estimating force required to perform the user steps at the grade; and improving the user mechanical work accuracy by estimating the mechanical work using the load.

In one aspect, the method comprises: receiving magnetic field data from a magnetic field sensor; the estimating the device heading comprising: determining a yaw component of rotational data generated from the acceleration data and the gyroscope data; and improving accuracy of the device heading by combining the yaw component with a second yaw component of a second rotational data generated from the magnetic field data. In one aspect, the yaw component of the rotational data is the rotational angle relative to a horizontal frame of reference.

In one aspect, disclosed herein a computer implemented methods for improving performance of a wearable device while recording a walking activity comprising: receiving motion data of a user from a motion sensing module of the wearable device; counting, by one or more processor circuits of the wearable device, user steps based on the motion data; detecting, by the one or more processor circuits, a bout based on the user steps, the bout comprising a collection of continuous steps; estimating, by the one or more processor circuits, user mechanical work performed during the bout; detecting, by the one or more processor circuits, the start of a walking activity, the detecting the start of the walking activity comprising: comparing the user mechanical work to a mechanical work threshold; in response to detecting a value for the user mechanical work that exceeds the mechanical work threshold, starting a walking activity; and sending, by the one or more processor circuits, a notification to the user requesting confirmation of the start of the walking activity.

In one aspect, the method comprises: receiving, pressure data, from a pressure sensor of the wearable device; receiving, location data, from a GPS module of the wearable device; calculating, by the one or more processor circuits, a grade for each step included in the user steps based on the pressure data, the grade measuring steepness of terrain stepped on during the bout; calculating, by the one or more processor circuits, a step distance for each step included in the bout based on the motion data and the location data; calculating, by the one or more processor circuits, a bout time describing the bout's duration; and estimating, by the one or more processor circuits, the user mechanical work performed during the bout based on the step distance, the grade, and the bout time.

In one aspect, the methods comprise: calculating, by the one or more processor circuits, load based on the grade and the user steps, the load estimating force required to perform the user steps at the grade; and improving the user mechanical work accuracy by estimating the mechanical work using the load. In one aspect, the method comprises: estimating, by the one or more processor circuits, a device heading at every step included in the bout based on the motion data, the device heading describing the orientation of the wearable device relative to a frame of reference; determining, by the one or more processor circuits, a user direction of travel based on the device heading and the step count; and classifying movement performed during the bout based on the user direction of travel.

In one aspect, the method comprises: receiving magnetic field data from a magnetic field sensor; the estimating the device heading comprising: determining a yaw component of rotational data generated from the acceleration data and the gyroscope data; and improving accuracy of the device heading by combining the yaw component with a second yaw component of a second rotational data generated from the magnetic field data. In one aspect, the yaw component of the rotational data is the rotational angle relative to a horizontal frame of reference. In one aspect, the method comprises: distinguishing between a walking workout and a casual walking activity based on the comparing the user mechanical work to the user mechanical work threshold.

In one aspect, disclosed herein are systems for improving performance of a wearable device while recording a walking activity comprising: a motion sensing module configured to collect a user's motion data; one or more processor circuits in communication with the motion sensing module and configured to execute instructions causing the processor circuits to: count user steps based on the motion data; detect a bout based on the user steps, the bout comprising a collection of continuous steps; estimate user mechanical work performed during the bout; detect the start of a walking activity, the detecting the start of the walking activity comprising: comparing the user mechanical work to a mechanical work threshold; in response to detecting a value for the user mechanical work below the mechanical work threshold, classifying movement performed by the user based on motion data; and in response to classifying the movement performed by the user as a patterned movement, starting a walking activity; and send a notification to the user requesting confirmation of the start of the walking activity.

BRIEF DESCRIPTION OF THE DRAWINGS

Various objectives, features, and advantages of the disclosed subject matter can be more fully appreciated with reference to the following detailed description of the disclosed subject matter when considered in connection with the following drawings, in which like reference numerals identify like elements.

DESCRIPTION

The present disclosure describes systems and methods of detecting the start of an outdoor walking workout. Separating walking workouts from casual walking activities is challenging because the walking motion performed in each type of walking activity is highly similar. Additionally, walking workouts may have lower levels of exertion than other workout activities. To distinguish between walking workouts and casual walking activities, methods of detecting the start of an outdoor walking workout infer the intent of the user based on one or more types of sensor data collected by the wearable device.

In various embodiments, user intent may be inferred based on the mechanical work performed by the user during the walking activity and/or the user's pattern of movement. For example, if a user performs sustained mechanical work or has a predictable direction of travel, workout intent may be inferred by the wearable device. If the user does not perform sustained mechanical work and has a random direction of travel, it is likely the user is out for a causal walk and is performing a walking motion without workout intent. Referring now to the figures, methods of detecting the start of an outdoor walking workout are described below and exemplary embodiments are shown in the figures. However, the disclosure is not limited to the embodiments shown in the figures and described below since not every variation of using sensor data to infer workout intent during a walking activity may be described in detail.

Figure 1:
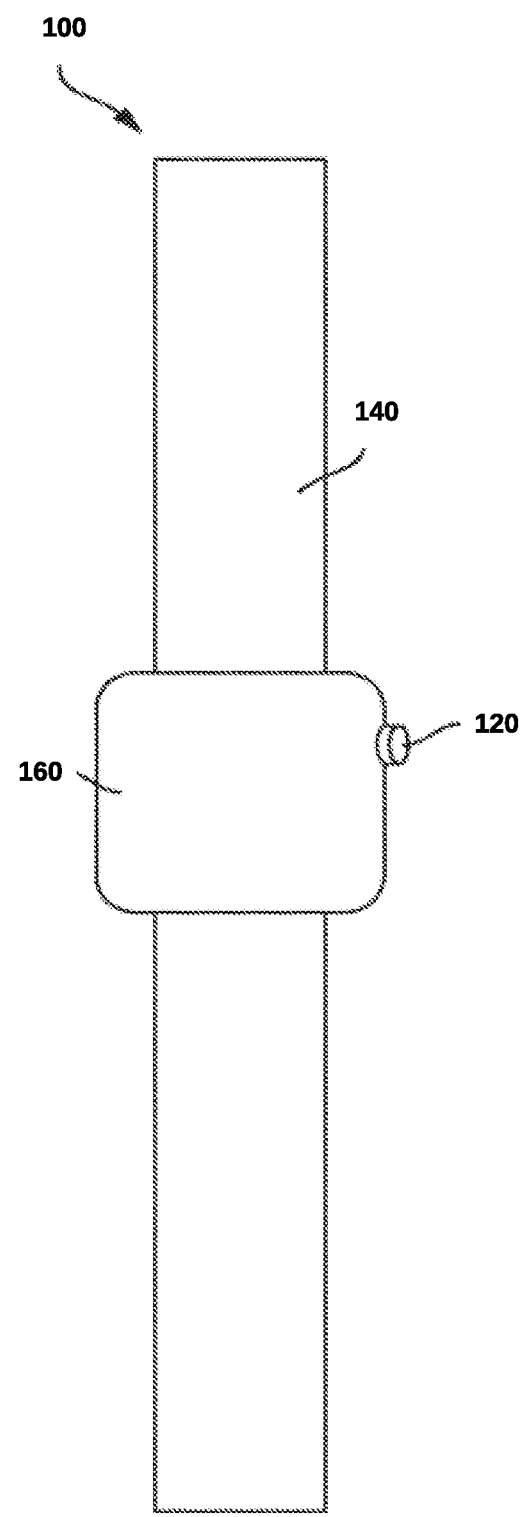
FIG. 1 is a diagram of an exemplary wearable device, according to embodiments of the disclosure.

FIG. 1 shows an exemplary wearable device 100 that may be worn by a user, in accordance with an embodiment of the present disclosure. In some embodiments, the wearable device 100 may be configured to be worn around the user's wrist using a strap 140 (e.g., a watch strap). The wearable device 100 may include one or more mechanisms for entering user inputs. For example, a crown 120 or other button configured to receive user inputs used to operate the wearable device 100. The wearable device 100 may include a display screen 160 for displaying information to a user.

As described in more detail below, the wearable device 100 may be configured to detect walking workouts performed by the user, record walking workouts, calculate performance information of the user during the walking workout, detect the type of walking activity (e.g., causal stroll, walking workout, and the like) performed by the user, and provide additional functionality related to walking activities to the user. In particular, the wearable device 100 may use motion data obtained from one or more motion sensors, heart rate data obtained from a heart rate sensing module, pressure data from one or more pressure sensors, and/or location data obtained from a GPS module to detect a walking movement and infer when the walking movement is a walking workout.

Figure 2:
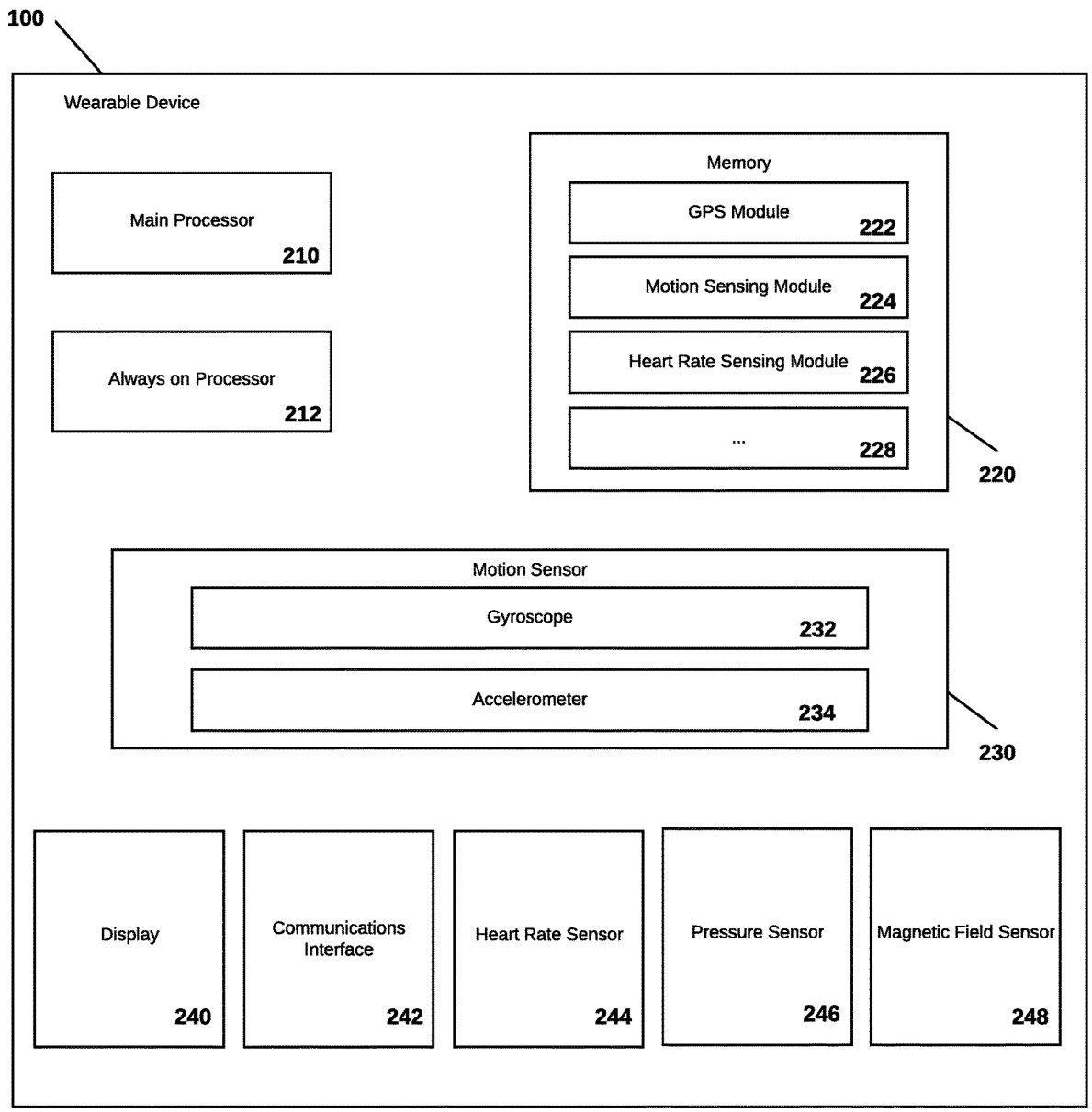
FIG. 2 is a block diagram showing exemplary components that may be found within a wearable device, according to embodiments of the disclosure.

FIG. 2 depicts a block diagram of exemplary components that may be found within the wearable device 100 according to some embodiments of the present disclosure. In some embodiments, the wearable device 100 can include a main processor 210 (or "application processor" or "AP"), an always on processor 212 (or "AOP" or "motion co-processor"), a memory 220, one or more motion sensors 230, a display 240, an interface 242, a heart rate sensor 244, and a pressure sensor 246, and a magnetic field sensor 248. The wearable device 100 may include additional modules, fewer modules, or any other suitable combination of modules that perform any suitable operation or combination of operations.

In some embodiments, main processor 210 can include one or more cores and can accommodate one or more threads to run various applications and modules. Software can run on main processor 210 capable of executing computer instructions or computer code. The main processor 210 can also be implemented in hardware using an application specific integrated circuit (ASIC), programmable logic array (PLA), field programmable gate array (FPGA), or any other integrated circuit.

In some embodiments, wearable device 100 can also include an always on processor 212 which may draw less power than the main processor 210. Whereas the main processor 210 may be configured for general purpose computations and communications, the always on processor 212 may be configured to perform a relatively limited set of tasks, such as receiving and processing data from motion sensor 230, heart rate sensor 244, pressure sensor 246, and other modules within the wearable device 100. In many embodiments, the main processor 210 may be powered down at certain times to conserve battery charge, while the always on processor 212 remains powered on. Always on processor 212 may control when the main processor 210 is powered on or off.

Memory 220 can be a non-transitory computer readable medium, flash memory, a magnetic disk drive, an optical drive, a programmable read-only memory (PROM), a read-only memory (ROM), or any other memory or combination of memories. Memory 220 can include one or more modules 222-228.

The main processor 210 and/or always on processor 212 can be configured to run one or more modules 222-228 stored in memory 220 that are configured to cause main processor 210 or always on processor 212 to perform various steps that are discussed throughout the present disclosure.

In some embodiments, the wearable device 100 can include one or more motion sensors 230. For example, motion sensors 230 can include a gyroscope 232 and an accelerometer 234. In some embodiments, accelerometer 234 may be a three-axis accelerometer that measures linear acceleration in up to three-dimensions (for example, x-axis, y-axis, and z-axis). In some embodiments, gyroscope 232 may be a three-axis gyroscope that measures rotational data, such as rotational movement, angular acceleration, and/or angular velocity, in up to three-dimensions (for example, yaw, pitch, and roll). In some embodiments, accelerometer 234 may be a microelectromechanical system (MEMS) accelerometer, and gyroscope 232 may be a MEMS gyroscope. Main processor 210 or always on processor 212 of wearable device 100 may receive motion information from one or more motion sensors 230 to track acceleration, rotation, position, and or orientation information of wearable device 100 in six degrees of freedom through three-dimensional space.

In some embodiments, the wearable device 100 may include other types of sensors in addition to accelerometer 234 and gyroscope 232. For example, the wearable device 100 may include a pressure sensor 246 (e.g., an altimeter, barometer, and the like), a magnetic field sensor 248 (e.g., a magnetometer, compass, and the like), and/or a location sensor (e.g., a Global Positioning System (GPS) sensor).

The wearable device 100 may also include a display 240. The display 240 may be a screen, such as a crystalline (e.g., sapphire) or glass touchscreen, configured to provide output to the user as well as receive input from the user via touch. For example, the display 240 may be configured to display a current heart rate or daily average energy expenditure. The display 240 may receive input from the user to select, for example, which information should be displayed, or whether the user is beginning a physical activity (e.g., starting a session) or ending a physical activity (e.g., ending a session), such as a walking session, a swimming session, a running session, or a cycling session. In some embodiments, wearable device 100 may present output to the user in other ways, such as by producing sound with a speaker, and wearable device 100 may receive input from the user in other ways, such as by receiving voice commands via a microphone.

In various embodiments, wearable device 100 may communicate with external devices via an interface 242, including a configuration to present output to a user or receive input from a user. The interface 242 may be a wireless interface. The wireless interface may be a standard Bluetooth® (IEEE 802.15) interface, such as Bluetooth® v4.0, also known as "Bluetooth low energy." In various embodiments, the interface may operate according to a cellphone network protocol such as Long Term Evolution (LTE™) or a Wi-Fi (IEEE 802.11) protocol. In various embodiments, the interface 242 may include wired interfaces, such as a headphone jack or bus connector (e.g., Lightning®, Thunderbolt™, USB, etc.).

Wearable device 100 can measure an individual's current heart rate from a heart rate sensor 244. The heart rate sensor 244 may also be configured to determine a confidence level indicating a relative likelihood of an accuracy of a given heart rate measurement. In various embodiments, a traditional heart rate monitor may be used and may communicate with wearable device 100 through a near field communication method (e.g., Bluetooth).

In various embodiments, the wearable device 100 can include a photoplethysmogram (PPG) sensor. PPG is a technique for measuring a person's heart rate by optically measuring changes in the person's blood flow at a specific location. PPG can be implemented in many different types of devices in various forms and shapes. For example, a PPG sensor can be implemented in a wearable device 100 in the form of a wrist strap, which a user can wear around the wrist.

A PPG sensor may also be implemented on the underside of a wearable device 100. The PPG sensor can optically measure the blood flow at the wrist. Based on the blood flow information, the wearable device 100 can derive the person's heart rate.

The wearable device 100 may be configured to communicate with a companion device, such as a smartphone. In various embodiments, wearable device 100 may be configured to communicate with other external devices, such as a notebook or desktop computer, tablet, headphones, Bluetooth headset, etc.

The modules described above are examples, and embodiments of wearable device 100 may include other modules not shown. For example, some embodiments of wearable device 100 may include a rechargeable battery (e.g., a lithium-ion battery), a microphone array, one or more cameras, two or more speakers, a watchband, water-resistant casing or coating, etc. In some embodiments, all modules within wearable device 100 can be electrically and/or mechanically coupled together. In some embodiments, main processor 210 and or always on processor 212 can coordinate the communication among each module.

In various embodiments, the wearable device 100 may use sensed and collected motion information to predict a user's activity. Examples of activities may include, but are not limited to walking, running, cycling, swimming, skiing, cardio machine activities, and the like. Wearable device 100 may also be able to predict or otherwise detect when a user is stationary (e.g., sleeping, sitting, standing still, driving or otherwise controlling a vehicle, etc.). Wearable device 100 may use a variety of motion data, rotational data, and/or orientation data to predict a user's activity.

Wearable device 100 may use a variety of heuristics, algorithms, or other techniques to predict the user's activity and/or detect activity start and end points. In various embodiments, one or more machine learning techniques and/or predictive models trained to predict the user's activity and/or detect activity start and end points. Training the one or more predictive models may include surveying a plurality of datasets including motion data, rotational data, heart rate data, and the like collected during activities having a known activity type (e.g., walking workouts, casual walking activities, running activities, and the like). Wearable device 100 may also estimate a confidence level (e.g., percentage likelihood, degree of accuracy, etc.) associated with a particular prediction (e.g., 90% likelihood that the user is cycling) or predictions (e.g., 60% likelihood that the user is cycling and 40% likelihood that the user is performing some other activity).

Figure 3:
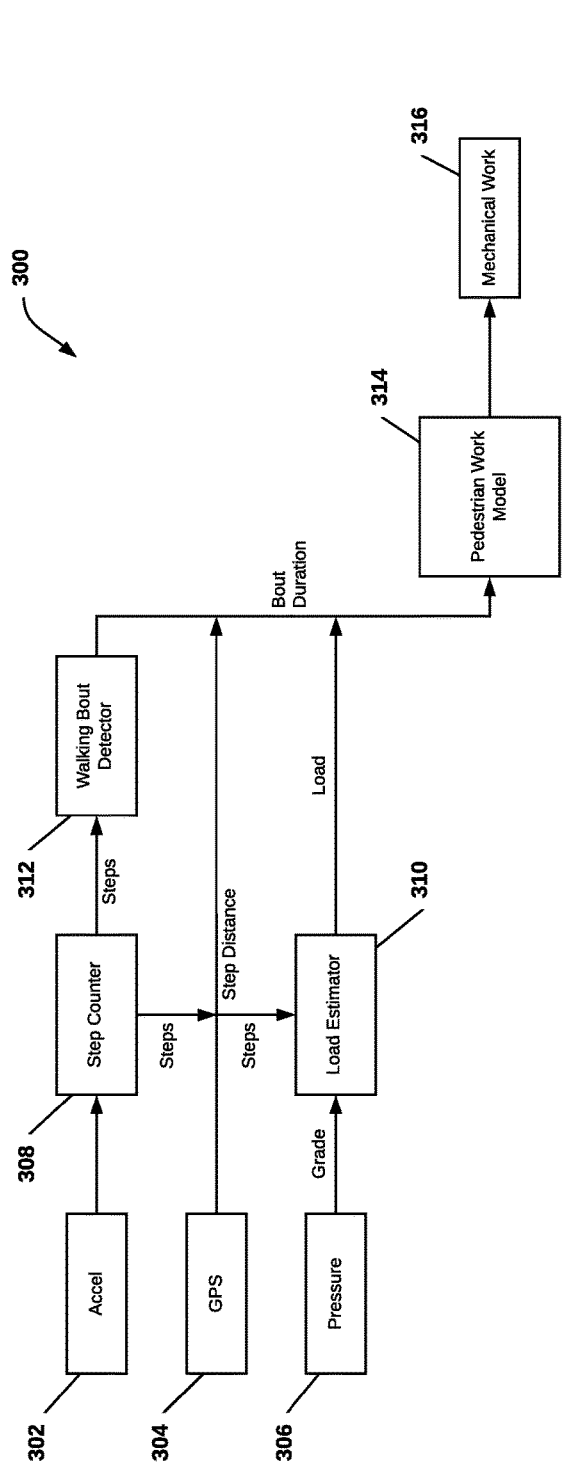
FIG. 3 is a flow chart illustrating an exemplary process of estimating mechanical work, according to embodiments of the disclosure.

FIG. 3 shows an exemplary process 300 for determining mechanical work of a user during a walking activity. To determine the mechanical work of a user, motion data may be measured by one or more motion sensors. Motion data may include accelerometer data 302 provided by an accelerometer, gyroscope data provided by a gyroscope, and magnetic field information provided by a magnetic field sensor. Rotational data (e.g., angular velocity, angular acceleration, a device position, etc.) may also be calculated from motion data and used to determine the mechanical work. In some embodiments, a step count and/or step rate ("Steps") may be determined by a step counter 308 or other pedometer function of the wearable device. For example, the step counter 308 may determine a step count based on motion features extracted from motion data and or rotational data that indicate steps. The motion features that indicate steps may be determined by surveying a plurality of datasets including motion data and or rotational data collected during known walking workouts. Motion features that are specific to a particular user may be determined by limiting the walking workouts included in the plurality of datasets to walking workouts performed by the particular user and or a group of users having one or more characteristics (e.g., age, height, stride length, fitness level, walking gait, and the like) in common with the particular user. The step rate can be used to detect a walking bout (e.g., a collection of continuous steps) performed by the user. For example, if a step rate exceeds a minimum step rate threshold for at least a bout threshold including minimum bout duration, the bout detector 312 may detect a bout. In various embodiments, a bout requires continuous steps for a defined period that exceeds the bout threshold, but there can be stops in between the steps as long as the stops are temporary. The minimum step rate threshold (e.g., 60 steps per minute) and or minimum bout duration (e.g., 5 minutes) included in the bout threshold by be determined by surveying a plurality of datasets include step rates and bout durations collected during walking activities having known bout starting and ending points. In response to detecting a bout, a pedestrian work model 314 may determine work performed by a user during the walking activity.

In various embodiments, step rate may be used to estimate the user's mechanical work 316. Step rate provides an indicator of how hard a user is working, for example, as step rate increases, the user may need to expend additional energy to maintain the higher step rate, therefore the user may do more work. Step rate may be a component of the mechanical work calculation performed by the pedestrian work model 314. Other factors used by the pedestrian work model 314 to estimate mechanical work performed by the user may include bout duration, step distance, and load (i.e., resistance).

Step distance may be determined based on GPS data 304, for example, latitude and longitude fixes. GPS data 304 may be provided by a GPS module that may triangulate three or more satellite signals to generate the fixes. In various embodiments, step distance may describe the distance traveled in each step counted by the step counter 308. Step distance may be estimated based on the step count and the total distance traveled during the walking activity. For example, dividing the total distance by the step count may generate an estimate for the average step distance.

The load or resistance may be based on the grade of the terrain traveled over during the walking activity. The grade may measure the steepness of terrain traversed during a bout (i.e., a collection of continuous steps) or other segment of the walking activity. In various embodiments, altimeter functionality such as estimating terrain grade or steepness, calculating elevation change, and/or determining relative altitude information may be implemented or otherwise determined from pressure data 306 measured by a pressure sensor of the wearable device. Load may indicate a user's mechanical work at each step. For example, walking over a steep grade requires more mechanical work than walking on flat ground. The load estimator 310 may estimate load by applying a load estimation model, e.g., a regression analysis or a decision tree analysis, to terrain grade and step rate information. For example, a relatively high terrain grade for a given step rate may indicate a relatively high load. To estimate load using terrain grade, the load estimator 310 may use a grade factor calculated by the wearable device. The grade factor may describe the resistance at a particular terrain grade and reflect the effort (e.g., work) required by the user to travel over a terrain having a particular grade.

In some embodiments, the load estimation model may account for a specific activity context. For example, in some activities, load or resistance may be a scaling factor for another variable such as speed. In some embodiments, the estimated load may be filtered using historical estimated load values (e.g., hysteresis) to smooth load estimation. For example, a load filter may limit the amount by which an estimated load may change from one time period to the next.

The pedestrian work model 314 can calculate the mechanical work 316 of a user during the walking activity. The pedestrian work model 314 may be specific to walking activities and the wearable device may include one or more alterative work models for calculating mechanical work of a user during a different activity type. For walking activities, the mechanical work can be calculated from the bout duration, load, step rate, and/or step distance. In various embodiments, mechanical work may be proximate to the amount of force required to move the load over the step distance within the bout duration. Mechanical work 316 generated by the pedestrian work model 314 may be output in Joules (J). The mechanical work of a user during the walking activity may be compared to a work threshold to infer user intent. In various embodiments, the mechanical work threshold may be specific to one or more user characteristics (e.g., age, gender, weight, body mass index (BMI), fitness level, and the like). For example, the mechanical work threshold for a fit person may be higher than the mechanical work threshold for an unfit person for the purposes of determining sustained work to indicate a walking activity. The mechanical work threshold may be determined by surveying a plurality of datasets including mechanical work calculated during walking activities having known period of casual walking (i.e., walking with no workout intent) and known periods of workout walking (i.e., walking with workout intent). A user specific mechanical work threshold may be determined by limiting the walking activities included in the plurality of datasets to walking activities performed by a particular user and or a group of users having one or more characteristics in common with the particular user. Mechanical work 316 may also be used to calculate work for the purposes of estimating caloric expenditure (in METs). For example, for a walking activity the mechanical work (WR) may be, WR=f(step rate)*g(grade), where f(·) denotes a function of the parameter(s) within parentheses.

Figure 4:
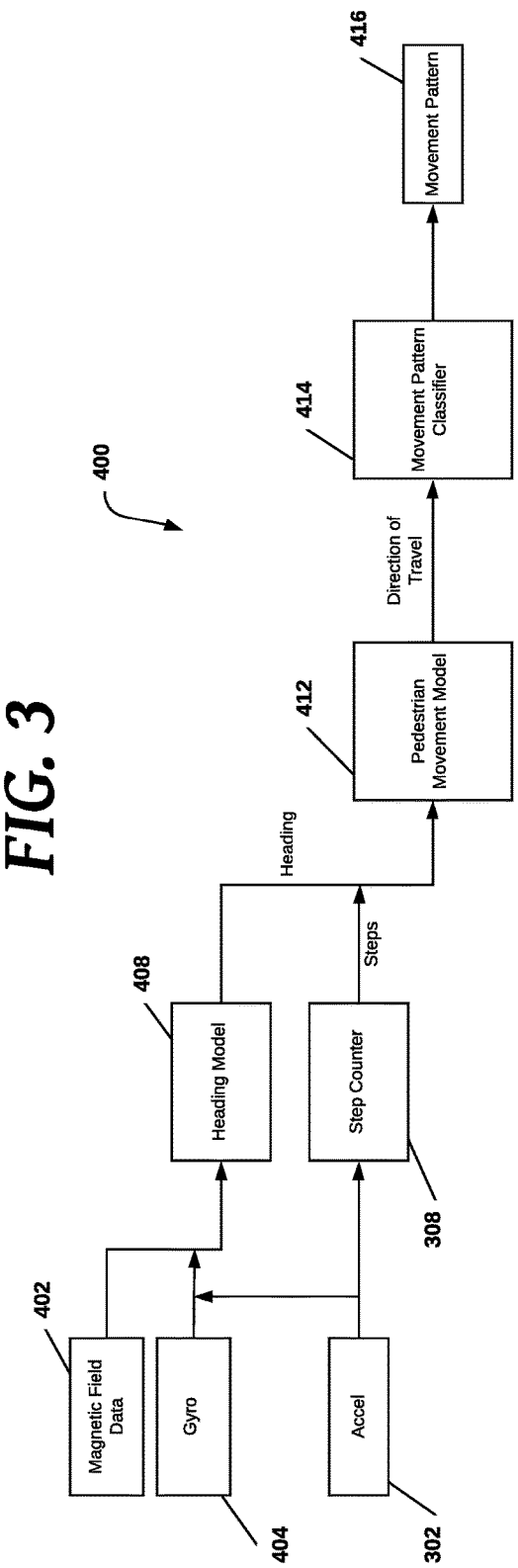
FIG. 4 is a flow chart illustrating an exemplary process of determining a movement pattern, according to embodiments of the disclosure.

FIG. 4 illustrates an exemplary process 400 of determining a movement pattern 416. In various embodiments, the movement pattern 416 may be an indicator of workout intent. For example, users having a predictable direction of travel indicated by a straight or repetitive movement pattern 416 are likely to be walking with workout intent. Therefore, movement patterns 416 generated from, for example, walking laps on a track or walking in the same general direction during a hike would be classified as repetitive movement patterns indicative of walking workouts. Movement patterns 416 generated from non-workout activities, for example, shopping, cleaning, cooking, and the like would be classified as random movement patterns indicating no workout intent.

To determine the movement pattern 416, the wearable device may use one or more types of sensor data. For example, the wearable device may use magnetic field data 402 received from a magnetic field sensor, gyroscope data 404 obtained from a gyroscope, and/or accelerometer data 302 obtained from an accelerometer to determine a user's movement pattern 416. Magnetic field data 402, gyroscope data 404, and acceleration data 302 may be input into a heading model 408. The heading model 408 may estimate a device heading using the input data. In various embodiments, the device heading may be determined by algorithmically combining accelerometer measurements 302 with gyroscope measurements 404 to provide a smoothed estimate of the orientation of the wearable device in three dimensional (3D) space relative to a frame of reference (e.g., a fixed body frame of reference, an inertial frame of reference, and the like). In various embodiments, magnetic field data 402 may also be used to determine the orientation of the wearable device in 3D space relative to a frame of reference (e.g., a fixed body frame of reference or an inertial frame) and or improve the accuracy of orientation estimates generated based on accelerometer measurements 302 and or gyroscope measurements.

To determine the orientation of the wearable device in 3D space, rotational data may be determined from motion data measured by the accelerometer, gyroscope, and or magnetic field sensor. Rotational data may include one or more angles relative an axis of rotational axis (e.g., roll, pitch, and yaw) that measure the angular displacement of the wearable device at a plurality of positions. Accelerometer 302 data, gyroscope data 404, and or magnetic field data 402 may be used to generate rotational data including three rotational angles for each sensor. The position of the wearable device may then be calculated by aggregating (e.g., averaging, normalizing, or otherwise combining) the rotational data generated by each sensor using 6 axis and or 9 axis sensor fusion. In various embodiments, device heading may then be calculated from the yaw component (e.g., rotational angle relative to the x axis or horizontal plane) of the rotational data. The yaw component of the rotational data may be a rotational angle in a frame of reference (e.g., an inertial frame or reference or a fixed body frame of reference). For example, in a fixed body frame of reference, the rotational angle included in the yaw component may describe the angular motion of the wearable device relative to an axis of rotation that is parallel to the display screen of the wearable device.

In various embodiments, magnetic field data 402 may be used to improve the accuracy of device headings by providing additional rotational data that describes the position of the wearable device in 3D space. For example, a horizontal angle of rotation (i.e., the yaw component of rotation—the angle of rotation relative to the x axis or horizontal plane in an inertial frame of reference or the angle of rotation relative to the axis parallel with the display screen of the wearable device in a fixed body frame of reference) may be calculated using rotational data generated from the magnetic field data 402. The horizontal angle of rotation generated from magnetic field data 402 may then be algorithmically combined (i.e., averaged, scaled, and the like) with the horizontal angles of rotation generated from gyroscope 404 data and accelerometer data 302 respectively to improve accuracy of device headings.

In various embodiments, the additional rotational datapoints based on magnetic field data can be used improve the accuracy of rotational data generated based on the accelerometer data 302 and gyroscope data 404. Rotational datapoints based on magnetic field data may normalize for integration drift and other errors that are commonly included in rotational data generated based on motion data. For example, the angular position or the angular velocity of the wearable device may be obtained based on the angular acceleration component of motion data by integrating the angular acceleration over time. Similarly, the angular position of the wearable device can be obtained based on the angular velocity by integrating the angular velocity over time. Therefore, generating rotational data based on motion data (i.e., angular acceleration and angular velocity) may require double integration of angular acceleration values and single integration of angular velocity values. Due to integration drift, rotational data based on angular acceleration and or angular velocity may be accurate for only relatively short time intervals (e.g., 30 seconds). The device orientation may be continuously tracked throughout a user's entire workout session (i.e., several minutes and or hours). Therefore, integration drift may diminish the accuracy of device orientation, device headings, relative heading, and other device position tracking estimates made throughout the duration of a full workout activity. By including datapoints based on magnetic field data in rotational data used to generate the device position tracking estimates, the device position tracking estimates used to determine user heading may be more accurate and consistent throughout the full workout activity.

The performance of the motion sensors included in the wearable device may also not be uniform across all device instances. Motion sensor calibration may be disturbed by significant shock events causing some motion sensors to have better calibration than others and some motion sensors to exhibit more drift in motion data. Rotational data generated based on magnetic field data may compensate for some of these common errors in rotational data derived from motion data. Magnetic field data describes the position of the wearable device relative to a steady state magnetic field near the device. The steady state magnetic field may be, for example, the earth's geomagnetic field, an ambient magnetic field generated by an electronic device or other aspects of the environment local to the wearable device, and the like. Determining rotational data based on magnetic field data does not require an integration operation. Thus, including datapoints derived from magnetic field data in rotational data can reduce the impact of integration drift. Accordingly, noise in rotational data based on motion data attributable to integration drift and inconsistent performance of motion sensors may be normalized by including rotational datapoints based on magnetic field data.

Similarly, noise in rotational data based on magnetic field data caused by, for example, a transient magnetic field generated by a mobile device passing in close proximity to the wearable device, may be normalized by using rotational data derived from motion data to determine the device position. Therefore, using motion data and magnetic field data to determine device position, device orientation, heading estimates, and other wearable device position tracking estimates, improves the precision, accuracy, and reliability of the device position tracking estimates generated by the wearable device.

In various embodiments, device headings generated by the heading model 408 may be combined with step count and/or step rate ("Steps") generated by a step counter 308. The step counter 308 may calculate steps based on accelerometer data 302 as described above in FIG. 3. To estimate a device direction of travel used to determine a movement pattern 416, the device headings and steps are input into a pedestrian movement model 412. The pedestrian movement model 412 may determine direction of travel and or changes in the direction of travel based on the change in device heading (e.g., relative device heading) during the walking activity. The pedestrian movement model 412 may estimate relative heading of the wearable device by calculating relative rotation data from the observed changes in acceleration 302 and/or gyroscope data 404 over time (i.e., calculating the difference in rotational data measured a first time point and rotational data measured at a second time point). The pedestrian movement model 412 may then calculate relative heading (i.e., the change in heading) from the relative rotational data. For example, the pedestrian movement model 412 may determine the relative rotational data by computing the difference in the angle of rotation relative to the wearable device's local horizontal plane. In a fixed body frame of reference, the device's local horizontal plane may be parallel to the direction of the crown, display screen or another component fixed to the surface of the wearable device. The pedestrian movement model 412 may then determine relative heading based on the horizontal component of the relative rotational data. The pedestrian movement model 412 may also determine a relative heading by determining the device heading at a first time point and a second time by then calculating the difference between the device headings. To accurately, track changes in user direction during the walking activity, the wearable device may continuously determine the device heading and or relative heading at a predetermined rate (e.g., every second, in real time (i.e., multiple times per second), every 10 seconds, every minutes, or any other rate of time). The accuracy of relative headings determined by the pedestrian movement model 412 may then be improved by incorporating more rotational data generated from magnetic field data 402 into device heading calculations.

In various embodiments, the relative headings are used to determine changes in user direction of travel. For example, the change in user direction may be indicated by the difference in the device heading at two different time points during the walking activity. To accurately identify changes in user direction throughout the walking activity, the wearable device may continuously determine relative device headings at a predetermined rate. Large relative heading values (e.g., relative heading values above a heading threshold i.e., 140 degrees) may indicate a change in direction because sustained, significant changes in the direction of travel of the user device (i.e., the device heading) correspond to changes in the direction of travel of the user. For example, if a user is walking north and turns around and starts walking south the yaw component of the rotational data of the wearable device worn by the user may change 180 degrees causing a 180 degree change in device heading. Constant relative heading values having little change over time may indicate a constant direction of travel. Relative heading values may be combined with steps to associate the direction of travel with the walking pace of the user.

The movement pattern classifier 414 may determine a movement pattern 416 based on the direction of travel and the steps during the walking activity. For example, walking movements having many different changes in direction and frequent changes of walking pace may have a random movement pattern. Walking movements having fewer changes in direction and a more consistent pace may have a patterned movement pattern. For example, walking movements having few changes in direction and changes of direction that do not repeat at regular time and or distance intervals and or a constant walking pace may have a straight movement pattern. Walking movements having changes in direction that repeat at regular time and or distance intervals during the walking activity and a constant walking pace may have a repetitive movement pattern. To determine the movement pattern 416, the movement pattern classifier 414 may classify a walking movement performed by the user.

To classify the walking movement, the movement pattern classifier 414 may compare the number of changes in direction and or walking pace (i.e., walking speed) calculated for a segment of a walking activity to a change of direction threshold and or expected walking speed. The number of changes in direction may be determined for a segment of a walking activity having any duration of time (i.e., the entire walking activity, 1 minute of the walking 5 minutes of the walking activity, or any other time period) or distance (i.e., 500 meters, 0.1 miles, 0.5 miles, 1 kilometer, or any other distance). If the number of changes in direction that occur during the segment of the walking activity exceeds the change of direction threshold (e.g., 9 changes in direction), the movement pattern classifier 414 may classify the walking movement performed during the segment as a random movement pattern. If the number of changes in direction that occur during the segment of the walking activity does not exceed the change of direction threshold, the movement pattern classifier 414 may classify the walking movement performed during the segment as a patterned movement (i.e., a straight movement pattern or a repetitive movement pattern). The number of changes of direction and the time and or distance when the changes of direction occur may be used to differentiate a straight movement pattern from a repetitive movement pattern. For example, if the changes of direction during the segment repeat at regular time and or distance intervals during the walking activity, the movement pattern classifier 414 may classify the walking movement as a repetitive movement pattern. If the changes of direction during the segment are well below (e.g., 80% to 90% below the changes in direction threshold) and or the changes of direction do not repeat at regular time and or distance intervals, the movement pattern classifier 414 may classify the walking movement as a straight movement pattern.

The number changes of direction included in the change of direction threshold used to detect a walking activity with workout intent (i.e., a walking activity having a straight and or repetitive movement pattern) and the magnitude of the relative heading included in the heading threshold used to detect a change of direction may be determined by surveying a plurality of datasets including motion data, rotational data, location data, pressure data, and other sensor data measured during walking activities having periods of known casual walking and known periods of workout walking. The plurality of datasets may also include device position measurements, device headings, relative headings, changes of direction, and other metrics measured from the sensor data. A user specific change of direction threshold and heading threshold may be determined by limiting the plurality of datasets to data collected during walking activities performed by the user and or a group of users having one or more characteristics in common with the user.

Figure 5:
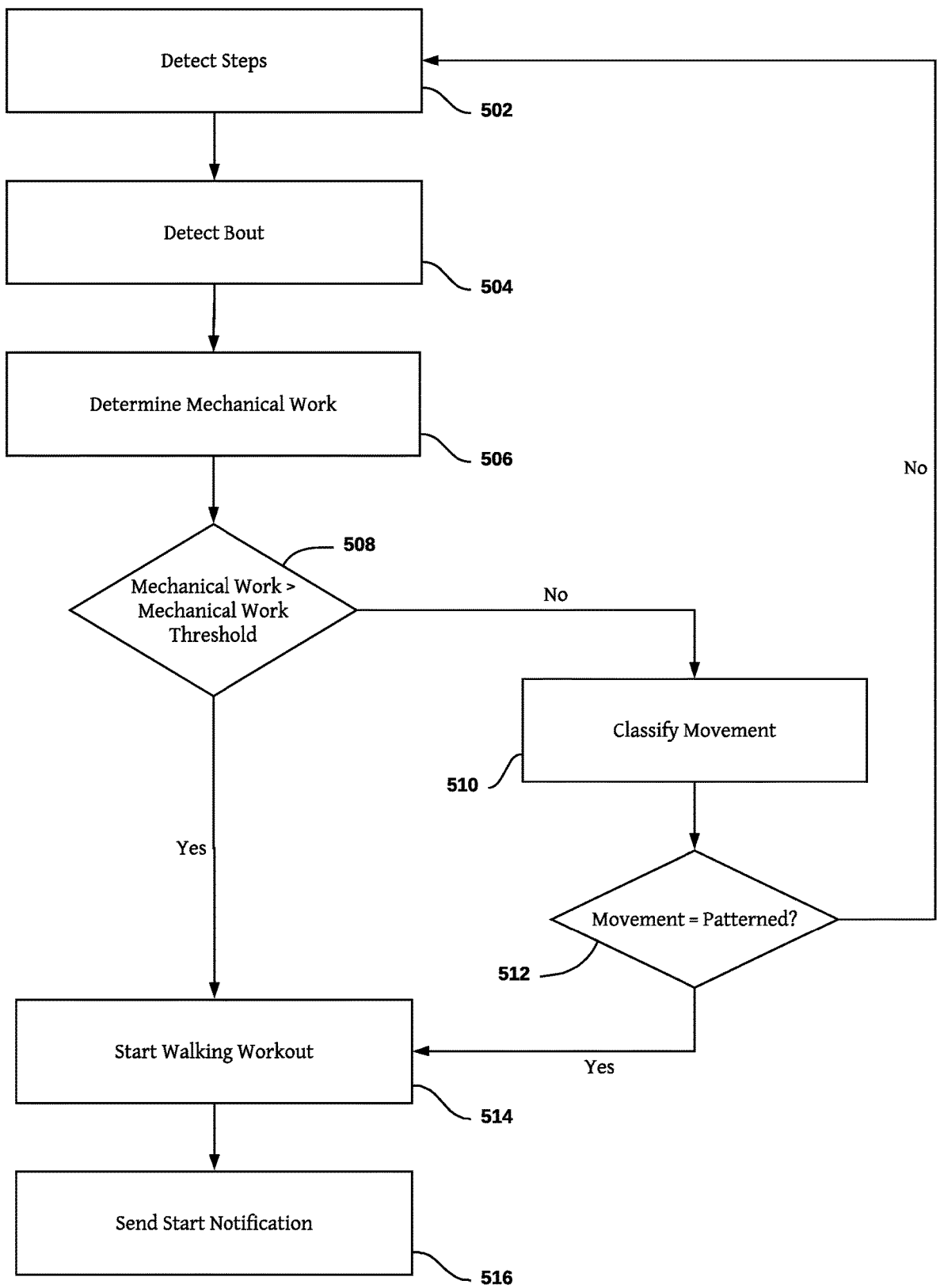
FIG. 5 is a flow chart illustrating an exemplary process of detecting the start of a walking workout, according to embodiments of the disclosure.

FIG. 5 illustrates and example method for detecting the start of a walking workout. At step 502, the wearable device determines the user is walking by detecting steps performed by the user. In various embodiments, the wearable device may detect steps based on motion data received from one or more motion sensors. In response to detecting steps, one or more pedometer functions of the wearable device may be activated to determine a user step count and/or step rate ("Steps") as described above in FIGS. 3-4. Based on the user steps, the wearable device may detect a bout at step 504. In various embodiments, the bout may be a collection of continuous steps performed during a predetermined period of time (e.g., 30 seconds, 1 minute, 5 minutes, 30 minutes, or any other length of time). The bout may have a minimum duration that corresponds to a bout threshold. To detect a bout, the walking bout detector described above in FIG. 3 may detect a plurality of continuous steps performed by a user for a sustained period of time that exceeds the bout threshold (e.g., 30 seconds, 1 minute, or any other period of time). In various embodiments, the bout detector may allow the wearable device to distinguish a casual walking motion (i.e., walking to the next room, walking down a flight of stairs, walking into a building from a car other transportation, standing, stretching, and any other walking motion that has no workout intent) from a workout walking motion (i.e., walking laps around a track, hiking, and any other walking motion that has workout intent).

At step 506, the wearable device may estimate mechanical work of the user during the bout as described above in FIG. 3. Mechanical work may then be used to detect a walking workout by determining if the user intends to perform a walking workout. In various embodiments, intent to perform a walking workout may be distinguished from intent to engage in a casual walking activity by detecting walking activities having sustained work and/or walking activities having a predictable direction of travel. In addition to estimating mechanical work, in response to detecting the walking bout, the wearable device may record a walking workout and calculate other types of performance information of the user during the bout. Performance information may include, mechanical work, work rate, energy expenditure, walking speed, heart rate, bout duration, distance traveled, calories burned, step count, step rate, and the like.

At step 508, mechanical work may then be compared to a mechanical work threshold to determine if the walking performed by the user is part of a walking workout or if the walking is causal walking. In various embodiments, if the mechanical work exceeds the mechanical work threshold for a predefined period of time (e.g., 30 seconds, 1 minute, 5 minutes, 15 minutes, or any other length of time) the wearable device may determine the user's work is sustained during the walking activity. The mechanical work threshold may correspond to any mechanical work value (e.g., 7.3 Joules per kilogram or any other value for mechanical work) and may be determined by surveying a plurality of datasets including motion data, pressure data, load data, steps, step rate, and or mechanical work measured during walking activities having known periods of casual walking and known periods of workout walking. A mechanical work threshold that is specific to a particular user may be determined by limiting the walking activities included in the plurality of datasets to walking activities performed by the particular user and or a group of users having one or more characteristics in common with the particular user.

In response to detecting a sustained level of work during the walking workout based on the user's mechanical work, the wearable device may start a walking workout at step 514. If the mechanical work does not exceed the mechanical work threshold, the wearable device may determine the user's work is not sustained and may perform additional analysis to determine if the user is performing a walking workout. For example, the wearable device may classify the movement during the walking activity at step 510.

The wearable device may classify the user's walking movement by generating a movement pattern as described above in FIG. 4. At step 512, the movement pattern is evaluated to determine if the user's direction of travel is predictable. In various embodiments, if the user's movement during the walking activity is patterned (e.g., straight or repetitive), the wearable device may determine the user has a predictable direction of travel while walking and may start the walking workout at step 514. If the user's movement during the walking activity is not patterned (e.g., is random), the wearable device may determine the user has an unpredictable direction of travel while walking and may repeat the analysis is steps 502-512 in response to detecting the next step motion performed by the user.

In response to detecting a walking workout by determining the user's work is sustained during the walking activity and/or the user has a predictable direction of travel, the wearable device may send a start notification to the user at step 516. In various embodiments, the start notification may be a UI displayed on a display screen of the wearable device. The UI may include a selectable option for confirming the start of the walking workout. An exemplary start notification UI is shown below in FIG. 7.

Figure 6:
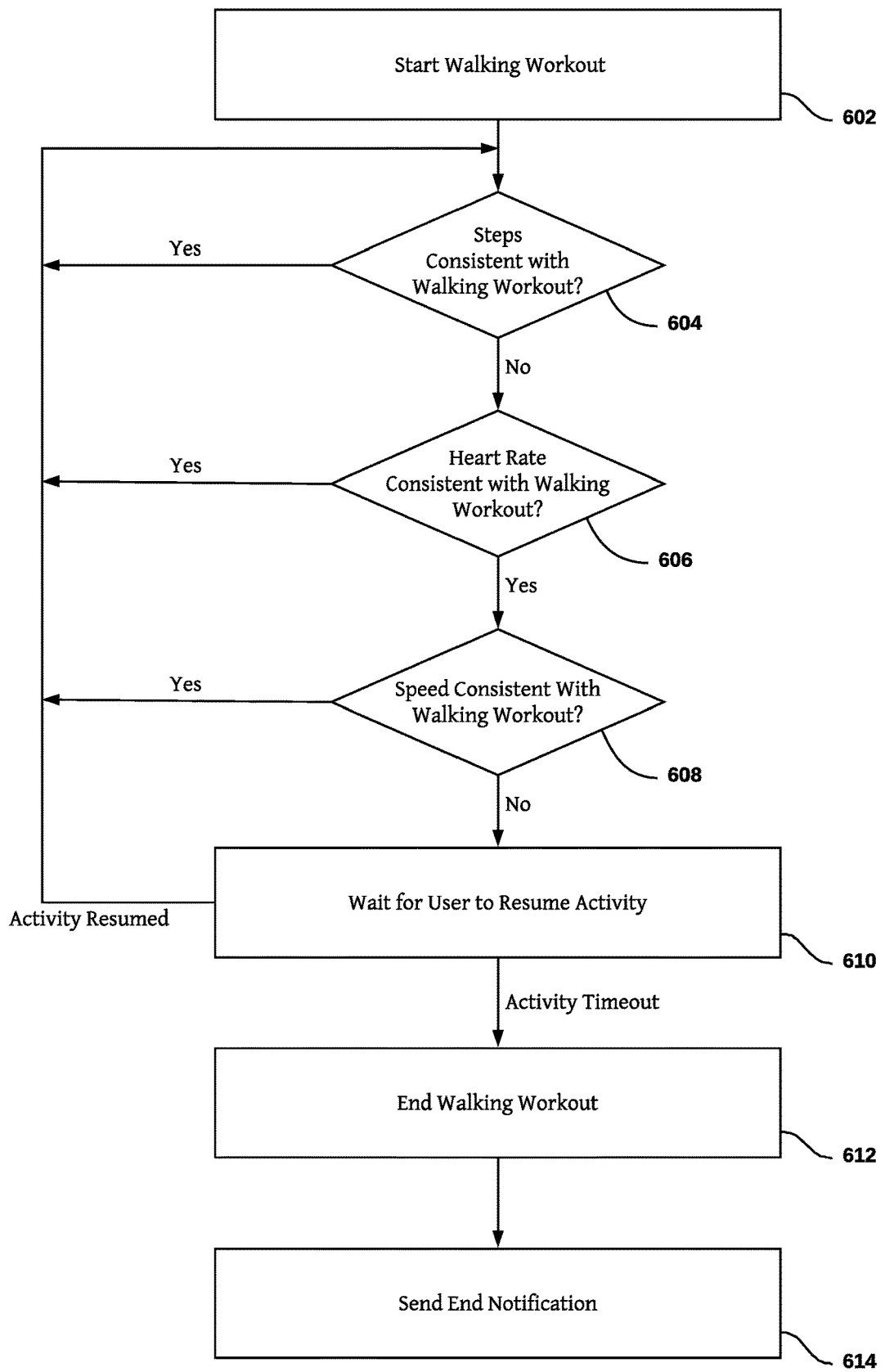
FIG. 6 is a flow chart illustrating an exemplary process of detecting the end of a walking workout, according to embodiments of the disclosure.

FIG. 6 illustrates an exemplary method for detecting the end of a walking workout. At step 602 a wearable device begins a walking workout. Once the wearable device starts the workout and begins recording the walking workout, user performance information including steps, heart rate, location data, and speed may be calculated by the wearable device. At steps 604-608, the wearable device then compares user performance information to one or more aspects of a walking workout profile. The walking workout profile may include one or more features of walking workouts, for example, expected steps (i.e., the number of steps performed during a predetermined period of time of a walking workout), expected heart rate (i.e., the heart rate of a user during a walking workout), and or expected speed (i.e., the walking speed of a user during a walking workout). The walking workout profile may be generated by surveying a plurality of datasets including motion data, pressure data, location data, magnetic field data, and other sensor data measured during walking activities that include known periods of causal walking and known periods of workout walking. The plurality of datasets may also include one or more pieces of data determined based on the sensor data, for example, rotational data, steps, step rate, load, mechanical work, heading, relative heading, and the like. A walking workout profile may be specific to a particular user. To determine the user specific walking workout profile, the walking activities included in the plurality of datasets may be limited to the particular user and or a group of users having one or more characteristics (e.g., weight, BMI, age, gender, fitness level, and the like) in common with the user.

At step 604, steps are calculated based on accelerometer data and or other motion data measuring during the walking workout. The steps may be calculated for the entire walking workout and or a predetermined portion of the walking workout (e.g., 30 seconds, 5 minutes, or any other time period). The steps calculated from motion data are then compared to the expected steps observed over the same time period. As described above, the expected steps may be determined by surveying a plurality of datasets including motion data and or calculated steps collected during known walking workouts. If the steps are consistent with the expected steps included in the walking activity profile (i.e., the steps measured during the walking workout are within a threshold percent difference of the expected steps), the walking activity may be maintained. If the steps are inconsistent with the expected steps included in the walking activity profile (i.e., the steps measured during the walking workout are not within a threshold percent difference of the expected steps) additional analysis may be performed on sensor data collected during the walking workout to detect the end of the walking workout. For example, the wearable device may perform analysis on the heart rate data at step 606 and or walking speed data at step 608.

The threshold percent difference between calculated steps and expected steps for a walking workout may be determined by surveying a plurality of datasets including motion data and or calculated steps collected during walking workouts performed by one or more users and walking workout profiles including the expected steps for walking workouts for the same one or more users. A threshold percent difference between the calculated and expected steps that is specific to a particular user may be determined by limiting the walking workouts and walking workout profiles included in the plurality of datasets to walking workouts performed by—and walking workout profiles associated with—the particular user and or a group of users having one or more characteristics in common with the particular user.

At step 606, user heart rate is calculated from heart rate data measured by a heart rate sensor. The user heart rate may be calculated for the entire walking workout and or a predetermined portion of the walking workout. The user heart rate is then compared to an expected heart rate included in the walking workout profile. As described above, the expected heart rate may be determined by surveying a plurality of datasets including heart rate data collected during walking workouts. If the calculated user heart rate is consistent with the expected heart rate (i.e., the calculated user heart rate is within a threshold percent difference of the expected heart rate), the walking workout may be maintained. If the calculated user heart rate is inconsistent with the expected heart rate included in the walking activity profile (i.e., the calculated user heart rate is not within a threshold percent difference of the expected heart rate), additional analysis may be performed to confirm the end of the walking workout. For example, the wearable device may perform analysis on walking speed data at step 608 to confirm the end of the walking workout.

The threshold percent difference between the calculated user heart rate and the expected user heart rate for a walking workout may be determined by surveying a plurality of datasets including heart rate data collected during walking workouts performed by one or more users and walking workout profiles including the expected heart rates for walking workouts for the same one or more users. A threshold percent difference for the calculated and expected heart rates that is specific to a particular user may be determined by limiting the walking workouts and walking workout profiles included in the plurality of datasets to walking workouts performed by—and walking workout profiles associated with—the particular user and or a group of users having one or more characteristics in common with the particular user.

At step 608, user walking speed is calculated using location data generated by a GPS module. For example, user walking speed may be determined based on the amount of time required for the user to travel from a first location measured by the GPS module to a second location measured by the GPS module. The user walking speed may be calculated for the entire walking workout and or a predetermined period of time and or distance (e.g., a distance of 500 m, 500 ft, 0.5 mi, and the like and or a time of 10 seconds, 1 minute, 15 minutes, and the like). As described above, the expected walking speed may be determined by surveying a plurality of datasets including speed data collected during walking workouts. The wearable device may determine an expected walking speed for a particular user by limiting the walking workouts included in the plurality of datasets to walking workouts performed by the particular user and or a group of users having one or more characteristics in common with the particular user. The walking speed is then compared to an expected walking speed included in the walking workout profile. If the walking speed is consistent with the expected walking speed (i.e., the calculated walking speed is within a threshold percent difference of the expected walking speed), the walking workout may be maintained. If the walking speed is inconsistent with the expected speed included in the walking activity profile (i.e., the calculated walking speed is not within a threshold percent difference of the expected walking speed), the wearable device may wait for an activity timeout at step 610.

The threshold percent difference between calculated walking speed and the expected walking speed may be determined by surveying a plurality of datasets including walking speed data collected during walking workouts performed by one or more users and walking workout profiles including the expected walking speed for walking workouts for the same one or more users. A threshold percent difference of the calculated and expected walking speed that is specific to a particular user may be determined by limiting the walking workouts and walking workout profiles included in the plurality of datasets to walking workouts performed by—and walking workout profiles associated with—the particular user and or a group of users having one or more characteristics in common with the particular user.

If an activity timeout is detected, the wearable device may end the walking workout at step 612. If the user resumes walking before an activity timeout, the walking workout may be maintained and steps 604-610 may be repeated until the end of a walking workout is detected. At step 614, in response to detecting the end of a walking workout, the wearable device may send an end notification to the user. In various embodiments, the end notification may be a UI displayed on a display screen of the wearable device. The UI may include a selectable option for confirming the end of the walking workout. An exemplary end notification UI is shown below in FIG. 8.

Figure 7:
FIG. 7 is an exemplary user interface (UI) for confirming the start of a walking workout, according to embodiments of the disclosure.
Figure 8:
FIG. 8 is an exemplary UI for confirming the end of a walking workout, according to embodiments of the disclosure.

FIGS. 7-8 illustrate exemplary UIs rendered on a wearable device. FIG. 7 illustrates a UI for notifying the user that the wearable device has started a walking workout. The start notification UI may be delivered to the user by the wearable device as a UI rendered on the display screen. As shown in FIG. 7, the start notification UI may include a walking icon, a start workout prompt, and a selection queue for selecting a workout type. To confirm the start of a walking workout and/or begin a walking workout, a user may select a "start walking workout" option from the selection queue. Once a user makes a selection, the wearable device begins a walking workout. In various embodiments, selecting a walking workout from the workout selection queue may trigger display of a location tracking request and/or begin the process of determining steps.

FIG. 8, illustrates a UI for notifying the user of the end of a walking workout. The UI may be delivered to the user by the wearable device as a UI rendered on the display screen. As shown in FIG. 8, the end notification UI may include a walking icon, an end workout prompt, and a selection queue for confirming the end of a workout and/or changing a workout type. In various embodiments, the end notification UI may be displayed on the wearable device in response to detecting the end of a walking workout. To confirm the end of a walking workout, a user may select the end walking workout option from the selection queue. In response to receiving the confirmation of the end of the walking workout from the user, the wearable device may stop recording the walking workout and may stop calculating user performance information. The wearable device may then display the performance information for the walking activity on the display screen.

The foregoing description is intended to convey a thorough understanding of the embodiments described by providing a number of specific exemplary embodiments and details involving activity detection, workout performance tracking, walking activity monitoring, and motion pattern classification. It should be appreciated, however, that the present disclosure is not limited to these specific embodiments and details, which are examples only. It is further understood that one possessing ordinary skill in the art, in light of known systems and methods, would appreciate the use of the invention for its intended purposes and benefits in any number of alternative embodiments, depending on specific design and other needs.

It is to be understood that the disclosed subject matter s not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods, and systems for carrying out the several purposes of the disclosed subject matter. Therefore, the claims should be regarded as including such equivalent constructions insofar as they do not depart from the spirit and scope of the disclosed subject matter.

As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

As used herein, the terms "and/or" and "at least one of" include any and all combinations of one or more of the associated listed items.

Certain details are set forth in the foregoing description and in FIGS. 1-8 to provide a thorough understanding of various embodiments of the present invention. Other details describing well-known structures and systems often associated with wearable devices, walking activities, activity end detection, workout performance tracking, walking activity monitoring, motion pattern classification, and the like, however, are not set forth below to avoid unnecessarily obscuring the description of the various embodiments of the present invention.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter.

The invention claimed is:

1. A method for improving performance of a wearable device while recording a walking workout, the method comprising:
   training, by a processor, a predictive model to detect start and end points of a walking workout, the training based on training data that includes motion data indicative of casual walking activities and walking workouts;
   measuring, by a motion sensing module of the wearable device, motion data of a user;

determining, by the processor circuit of the wearable device, a number of steps performed by the user based on the motion data;

detecting, by the processor circuit, a bout based on the number of steps performed by the user during a predetermined period of time, the bout including a plurality of continuous steps performed by the user;

detecting, by the processor circuit, a step rate based on the number of steps performed by the user during the predetermined period of time;

determining, by the processor circuit, mechanical work performed by the user during the bout, wherein the mechanical work is based on a pedestrian work model that is a function of at least the step rate and a load;

detecting, by the processor circuit, a start of the walking workout based on the mechanical work, wherein detecting the start of the walking workout includes:

comparing the mechanical work performed by the user to a mechanical work threshold;

detecting a value for the mechanical work performed by the user that is below the mechanical work threshold;

in response to detecting the value for the mechanical work performed by the user that is below the mechanical work threshold, determining, with the trained predictive model, a patterned movement indicative of walking based on the motion data;

in response to determining the patterned movement indicative of walking, starting the walking workout and recording, by the processor circuit, the walking workout.

2. The method of claim 1, wherein the detecting the start of the walking workout includes:

comparing the mechanical work to a mechanical work threshold; and starting the walking workout in response to detecting a value for the mechanical work that exceeds the mechanical work threshold.

3. The method of claim 1, wherein the patterned movement is a straight movement pattern or a repetitive movement pattern, wherein the straight movement pattern has a number of changes in user direction below a change in direction threshold and one or more changes in user direction do not repeat at regular time or distance intervals; and the repetitive movement pattern has a number of changes in user direction below the change in direction threshold and one or more changes in user direction that repeat at regular time or distance intervals.

4. The method of claim 1, comprising:

sending, by the processor circuit, a notification to the user requesting confirmation of the start of the walking workout.

5. The method of claim 4, wherein the notification is a notification user interface displayed on a display screen of the wearable device.

6. The method of claim 1, comprising:

measuring, by a pressure sensor of the wearable device, pressure data;

measuring, by a GPS module of the wearable device, location data of the user;

determining, by the processor circuit, a grade for each step included in the number of steps based on the pressure data, the grade measuring steepness of terrain traversed during the bout;

determining, by the processor circuit, a step distance for each step included in the bout based on the motion data and the location data;

determining, by the processor circuit, a bout time describing a duration of the bout; and determining, by the processor circuit, the mechanical work performed during the bout based on the step distance, the grade, and the bout time.

7. The method of claim 6, comprising:

calculating, by the processor circuit, a load based on the grade and the number of steps performed by the user, the load estimating a force required to perform the number of steps over the grade; and improving, by the processor circuit, an accuracy of the mechanical work by estimating the mechanical work using the load.

8. The method of claim 1, comprising:

estimating, by the processor circuit, a device heading at every continuous step included in the bout based on the motion data, the device heading describing an orientation of the wearable device relative to a frame of reference;

determining, by the processor circuit, a number of changes in user direction based on the device heading and the number of steps; and classifying a walking movement performed during the bout based on the number of changes in user direction.

9. The method of claim 8, comprising:

measuring, by a magnetic field sensor of the wearable device, magnetic field data; and the estimating the device heading including:

determining rotational data based on the magnetic field data;

selecting a first yaw component of the rotational data determined based on the magnetic field data;

determining rotational data based on the motion data;

selecting a second yaw component of the rotational data determined based on the motion data; and improving accuracy of the device heading by determining the device heading based on a combination of the first yaw component and the second yaw component.

10. The method of claim 9, wherein at least one of the first yaw component of the rotational data determined based the magnetic field data and the second yaw component of the rotational data determined based on the motion data is a rotational angle in a fixed body frame of reference, wherein the rotational angle describes angular motion relative to an axis of rotation that is parallel to a display screen of the wearable device.

11. The method of claim 1, wherein the motion data comprises acceleration data obtained from an accelerometer and gyroscope data obtained from a gyroscope.

12. The method of claim 1, comprising:

distinguishing, by a processor circuit, between a walking workout and a casual walking activity based on comparing the mechanical work to a mechanical work threshold and classifying a walking movement performed by the user.

13. The method of claim 1, comprising:

in response to recording the walking workout, calculating, by the processor circuit, user performance information during the walking workout; and detecting, by the processor circuit, an end of the walking workout based the user performance information.

14. A system for improving performance of a wearable device while recording a walking workout, the system comprising:

a motion sensing module configured to measure motion data of a user; and a processor circuit in communication with the motion sensing module and configured to execute instructions causing the processor circuit to:
    train a predictive model to detect start and end points of a walking workout, the training based on training data that includes motion data indicative of casual walking activities and walking workouts;
    determine a number of steps performed by the user based on the motion data;
    detect, by the processor circuit, a bout based on the number of steps performed by the user during a predetermined period of time, the bout including a plurality of continuous steps performed by the user;
    detect a step rate based on the number of steps performed by the user during the predetermined period of time;
    determine mechanical work performed by the user during the bout, wherein the mechanical work is based on a pedestrian work model that is a function of at least the step rate and a load;
    compare the mechanical work performed by the user to a mechanical work threshold;
    detect a value for the mechanical work performed by the user that is below the mechanical work threshold;
    in response to detecting the value for the mechanical work performed by the user that is below the mechanical work threshold, determine, with the trained predictive model, a patterned movement indicative of walking based on the motion data;
    in response to determining the patterned movement indicative of walking, start the walking workout; and
    record the walking workout.

15. The system of claim 14, wherein the processor circuit is further configured to:
    compare the mechanical work to a mechanical work threshold; and
    determine the start of the walking workout in response to detecting a value for the mechanical work that exceeds the mechanical work threshold.

16. The system of claim 14, wherein the patterned movement is a straight movement pattern or a repetitive movement pattern, wherein the straight movement pattern has a number of changes in user direction below a change in direction threshold and one or more changes in user direction do not repeat at regular time or distance intervals; and the repetitive movement pattern has a number of changes in user direction below the change in direction threshold and one or more changes in user direction that repeat at regular time or distance intervals.

17. The system of claim 14, wherein comprising:
    a pressure sensor configured to measure pressure data;
    a module configured to measure location data of the user; and
    wherein the processor circuit is in communication with the pressure sensor and the module and the processor circuit is further configured to:
        determine a grade for each step included in the number of steps based on the pressure data, the grade measuring steepness of terrain traversed during the bout;
        determine a step distance for each step included in the bout based on the motion data and the location data;
        determine a bout time describing a duration of the bout; and
        determine the mechanical work performed during the bout based on the step distance, the grade, and the bout time.

18. The system of claim 17, wherein the processor circuit is further configured to:
    calculate a load based on the grade and the number of steps performed by the user, the load estimating a force required to perform the number of steps over the grade; and
    improve an accuracy of the mechanical work by estimating the mechanical work using the load.

* * * * *

UNITED STATES PATENT AND TRADEMARK OFFICE
CERTIFICATE OF CORRECTION

PATENT NO. : 12,109,453 B2
APPLICATION NO. : 17/032933
DATED : October 8, 2024
INVENTOR(S) : Gunes Dervisoglu et al.

It is certified that error appears in the above-identified patent and that said Letters Patent is hereby corrected as shown below:

In the Claims

Column 20, Line 41, In Claim 10, delete "based the" and insert -- based on the --; and Column 20, Line 62, In Claim 13, delete "based the" and insert -- based on the --.

Signed and Sealed this
Twenty-sixth Day of November, 2024

Katherine Kelly Vidal
*Director of the United States Patent and Trademark Office*